United States Patent
Bock et al.

(10) Patent No.: US 9,051,326 B2
(45) Date of Patent: Jun. 9, 2015

(54) PYRAZOLINE DERIVATIVES AND THEIR USE AS SELECTIVE ANDROGEN RECEPTOR MODULATORS

(75) Inventors: Mark Gary Bock, Boston, MA (US); Bharat Lagu, Acton, MA (US); Chetan Pandit, Karnataka (IN); Sanjita Sasmal, Hyderabad (IN); Thomas Ullrich, Bottmingen (CH)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/234,599

(22) PCT Filed: Jul. 25, 2012

(86) PCT No.: PCT/IB2012/053795
§ 371 (c)(1),
(2), (4) Date: Jul. 18, 2014

(87) PCT Pub. No.: WO2013/014627
PCT Pub. Date: Jan. 31, 2013

(65) Prior Publication Data
US 2014/0329876 A1    Nov. 6, 2014

(30) Foreign Application Priority Data
Jul. 27, 2011    (IN) .......................... 2140/DEL/2011

(51) Int. Cl.
| A61K 31/415 | (2006.01) |
|---|---|
| A61K 31/4162 | (2006.01) |
| C07D 231/54 | (2006.01) |
| C07D 487/04 | (2006.01) |

(52) U.S. Cl.
CPC .......... *C07D 487/04* (2013.01); *A61K 31/4162* (2013.01)

(58) Field of Classification Search
CPC . C07D 487/04; C07D 231/54; A61K 31/4162
USPC ....................................... 514/407; 548/363.1
See application file for complete search history.

(56) References Cited

U.S. PATENT DOCUMENTS
5,292,742 A    3/1994 Venkatesan

FOREIGN PATENT DOCUMENTS
| WO | 03/096980 | 11/2003 |
|---|---|---|
| WO | 2007/092727 | 8/2007 |

*Primary Examiner* — Samantha Shterengarts
(74) *Attorney, Agent, or Firm* — John B. Alexander

(57) ABSTRACT

The invention relates to a compound of formula (I) in free form or in pharmaceutically acceptable salt form (I), in which the substituents are as defined in the specification; to compounds of formula (I) for use as androgen receptor modulators. The present invention further provides a combination of pharmacologically active agents and a pharmaceutical composition.

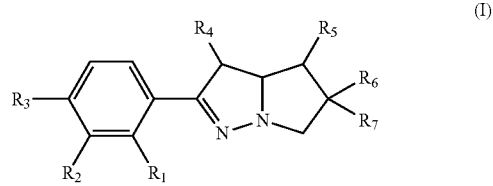

15 Claims, 1 Drawing Sheet

Figure 1: Effect of compound of example 1 on levator ani muscle and prostate wet weights
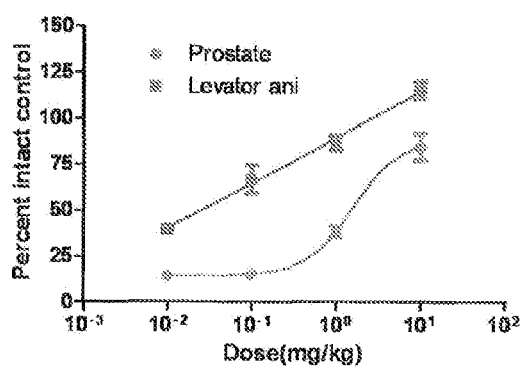
Figure 2: Effect of compound of example 5 on levator ani muscle and prostate wet weights
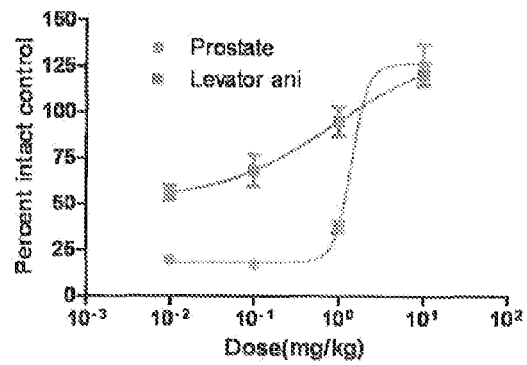

PYRAZOLINE DERIVATIVES AND THEIR USE AS SELECTIVE ANDROGEN RECEPTOR MODULATORS

This application is a U.S. National Phase filing of International Application No. PCT/IB2012/053795 filed 25 Jul. 2012, which claims priority to Indian Application No. 2140/DEL/2011 filed 27 Jul. 2011, the contents of which are incorporated herein by reference in their entirety.

The invention relates to pyrazoline derivative compounds, to their preparation, to their medical use as selective androgen receptor modulators and to medicaments, pharmaceutical compositions and combinations comprising them.

Selective androgen receptor modulators (SARMs) are ligands of the androgen receptor (AR) that have differential tissue regulation of AR. Selective androgen receptor modulators have been developed in the last decade as a new class of androgen receptor ligands analogous to androgenic drugs such as testosterone. Their improved selectivity over anabolic steroids suggests that this class of drugs could be developed for a number of therapeutic applications (Segal, S.; Narayanan, R.; Dalton J. T. Expert Opin. Investig. Drugs, 2006, 15(4), 377-387).

WO2003/096980 discloses certain bicyclic modulators of androgen receptor function. WO2006/076317 relates to aminophenyl derivatives which are selective androgen receptor modulators.

There is a continuing need to develop new modulators of the androgen receptor that are good drug candidates. SARMs would find wide application in conditions such as muscle wasting diseases, osteoporosis, sarcopenia, frailty, and cancer cachexia in both men and women. In contrast to an androgen, a desirable property of a SARM is that it would have an agonistic effect on the skeletal muscle and would be antagonistic or inactive in the prostate for example.

Compounds of the invention are selective for anabolic effect in e.g. muscle and bone tissue, and may show beneficial effects in CNS while only having very limited androgenic effects in e.g. prostate and skin. The compounds of the invention show low affinity for other receptors. Particular compounds of the invention possess favourable pharmacokinetic properties, are non-toxic and demonstrate few side-effects. Furthermore, the ideal drug candidate will exist in a physical form that is stable, non-hygroscopic and easily formulated.

The compounds of the invention are selective androgen receptor modulators. They are therefore potentially useful in the treatment of a wide range of disorders or diseases, particularly muscle wasting diseases, osteoporosis, sarcopenia, frailty, and cancer cachexia.

The invention therefore provides a compound of formula (I) in free form or in pharmaceutically acceptable salt form,

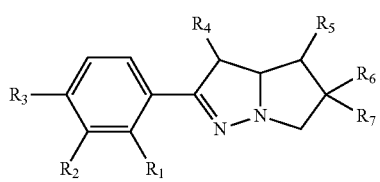

(I)

wherein
$R_1$ is $C_1$-$C_3$alkyl;
$R_2$ is halogen;
$R_3$ is cyano;
$R_4$ is selected from amino, halogen, hydroxy, $C_1$-$C_3$alkyl, halogen-$C_1$-$C_3$alkyl, hydroxy-$C_1$-$C_3$alkyl, $C_3$-$C_6$cycloalkyl, $C_1$-$C_3$alkoxy, halogen-$C_1$-$C_3$alkoxy, $C_1$-$C_3$alkoxy-$C_1$-$C_3$alkoxy, $C_3$-$C_6$cycloalkyl-$C_1$-$C_3$alkoxy, $C_3$-$C_6$cycloalkoxy; or $R_4$ is selected from a (=O), (=S) or (=N($R_8$)) group;

$R_5$ is selected from hydrogen, amino, halogen, hydroxy, $C_1$-$C_3$alkyl, halogen-$C_1$-$C_3$alkyl, hydroxy-$C_1$-$C_3$alkyl, $C_3$-$C_6$cycloalkyl, $C_1$-$C_3$alkoxy, halogen-$C_1$-$C_3$alkoxy, $C_3$-$C_6$cycloalkoxy; or $R_5$ is selected from a (=O), (=S) or (=N($R'_8$)) group;

$R_6$ is selected from hydrogen, amino, halogen, hydroxy, $C_1$-$C_3$alkyl, halogen-$C_1$-$C_3$alkyl, $C_3$-$C_6$cycloalkyl, $C_1$-$C_3$alkoxy, halogen-$C_1$-$C_3$alkoxy, $C_3$-$C_6$cycloalkoxy;

$R_7$ is selected from hydrogen, halogen, halogen-$C_1$-$C_3$alkyl;

or $R_6$ and $R_7$ together with the carbon to which they are attached form a —C(=O)— or —C(=S)— group;

$R_8$ and $R'_8$ are independently selected from hydrogen, hydroxy;

provided $R_5$, $R_6$, and $R_7$ are not all hydrogen.

FIGS. 1 and 2 both show the effect of compounds of the invention on levator ani muscle weight gain versus prostate wet weight gain in male Wistar rats.

Unless specified otherwise, the term "compounds of the present invention" refers to compounds of formula (I), (Ia), (Ib), (Ic) and (Id), salts of the compound, hydrates or solvates of the compounds and their salts, as well as all stereoisomers (including diastereoisomers and enantiomers), tautomers and isotopically labeled compounds (including deuterium substitutions), as well as inherently formed moieties (e.g., polymorphs, solvates and/or hydrates).

As used herein, the term "alkyl" refers to a fully saturated branched or unbranched hydrocarbon moiety having up to 3 carbon atoms. Unless otherwise provided, alkyl refers to hydrocarbon moieties having 1 to 3 carbon atoms. Representative examples of alkyl include, but are not limited to, methyl, ethyl, n-propyl, iso-propyl.

As used herein, the term "haloalkyl" refers to an alkyl as defined herein that is substituted by one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

As used herein, the term "alkoxy" refers to alkyl-O—, wherein alkyl is defined herein above. Representative examples of alkoxy include, but are not limited to, methoxy, ethoxy, propoxy, 2-propoxy. Typically, alkoxy groups have 1-3 carbons.

As used herein, the term "cycloalkyl" refers to saturated monocyclic hydrocarbon groups of 3-6 carbon atoms or unsaturated monocyclic hydrocarbon groups of 5 or 6 carbons. Exemplary monocyclic hydrocarbon groups include, but are not limited to, cyclopropyl, cyclobutyl, cyclopentyl, cyclopentenyl, cyclohexyl and cyclohexenyl and the like.

As used herein, the term "cycloalkoxy" refers to cycloalkyl-O—, wherein cycloalkyl is defined herein above.

Representative examples of cycloalkoxy include, but are not limited to, cyclopropyloxy, cyclobutyloxy, cyclopentyloxy, cyclohexyloxy and the like.

As used herein, the term "halogen" or "halo" refers to fluoro, chloro, bromo, and iodo.

Typically, the term "selective androgen receptor modulators (SARMs)" includes compounds which are, for example, selective agonists, partial agonists, antagonists or partial antagonists of the androgen receptor.

Typically, the term "modulator" refers to a chemical compound with capacity to either enhance (e.g. "agonist" activity) or inhibit (e.g. "antagonist" activity) a functional property of biological activity or process (e.g. enzyme activity or receptor binding); such enhancement or inhibition may be contingent on the occurrence of a specific event, such as regulation of a signal transduction pathway, and/or may be manifest only in particular cell types.

Various embodiments of the invention are described herein. It will be recognized that features specified in each embodiment may be combined with other specified features to provide further embodiments.

In one embodiment, the invention provides a compound of formula (I) in free form or in pharmaceutically acceptable salt form as described above.

In one embodiment, the invention relates to a compound of formula (Ia) in free from or in pharmaceutically acceptable salt form

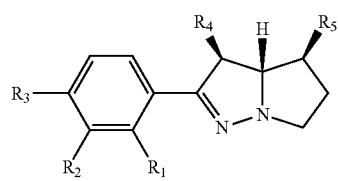

(Ia)

wherein $R_1$, $R_2$, $R_3$, $R_4$ and $R_5$ are as defined in relation to a compound of formula (I), wherein $R_5$ is not hydrogen.

In one embodiment, the invention relates to a compound of formula (Ib) in free form or in pharmaceutically acceptable salt form

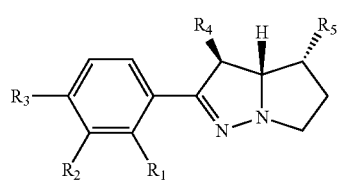

(Ib)

wherein $R_1$, $R_2$, $R_3$, $R_4$ and $R_5$ are as defined in relation to a compound of formula (I), wherein $R_5$ is not hydrogen.

In one embodiment, the invention relates to a compound of formula (Ic) in free from or in pharmaceutically acceptable salt form

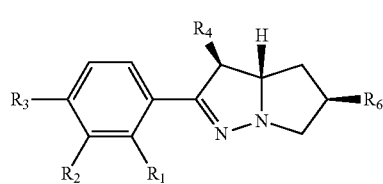

(Ic)

wherein $R_1$, $R_2$, $R_3$, $R_4$ and $R_6$ are as defined in relation to a compound of formula (I), wherein $R_6$ is not hydrogen.

In one embodiment, the invention relates to a compound of formula (Id) in free form or in pharmaceutically acceptable salt form

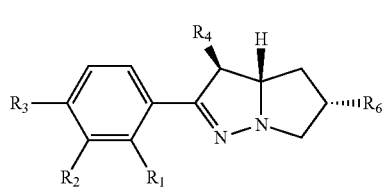

(Id)

wherein $R_1$, $R_2$, $R_3$, $R_4$ and $R_6$ are as defined in relation to a compound of formula (I), wherein $R_6$ is not hydrogen.

In certain embodiments, the invention relates to a compound of formula (I), (Ia), (Ib), (Ic) or (Id) in free form or in pharmaceutically acceptable salt form, in which:
(1) $R_1$ is $C_1$-$C_3$ alkyl;
(2) $R_1$ is methyl;
(3) $R_2$ is halogen;
(4) $R_2$ is chloro;
(5) $R_4$ is amino, halogen, hydroxy, $C_1$-$C_3$alkyl, halogen-$C_1$-$C_3$-alkyl, hydroxy-$C_1$-$C_3$-alkyl, $C_3$-$C_6$cycloalkyl, $C_1$-$C_3$alkoxy, halogen-$C_1$-$C_3$-alkoxy, $C_1$-$C_3$alkoxy-$C_1$-$C_3$alkoxy, $C_3$-$C_6$cycloalkyl-$C_1$-$C_3$alkoxy, $C_3$-$C_6$cycloalkoxy; or $R_4$ is selected from a (=O), (=S), (=NH) or (=N(OH)) group;
(6) $R_4$ is hydroxy, $C_1$-$C_3$alkyl, halogen-$C_1$-$C_3$-alkyl, $C_1$-$C_3$-alkoxy, halogen-$C_1$-$C_3$-alkoxy; or $R_4$ is selected from a (=O) group;
(7) $R_4$ is hydroxy, $C_1$-$C_3$alkyl, $C_1$-$C_3$-alkoxy or halogen-$C_1$-$C_3$-alkoxy;
(8) $R_4$ is hydroxy;
(9) $R_4$ is methyl;
(10) $R_4$ is ethyl;
(11) $R_4$ is methoxy;
(12) $R_4$ is ethoxy;
(13) $R_4$ is isopropyloxy;
(14) $R_4$ is fluoroethoxy;
(15) for a compound of formula (I), $R_5$ is hydrogen, amino, halogen, hydroxy, $C_1$-$C_3$alkyl, halogen-$C_1$-$C_3$-alkyl, hydroxy-$C_1$-$C_3$-alkyl, $C_3$-$C_6$cycloalkyl, $C_1$-$C_3$alkoxy, halogen-$C_1$-$C_3$-alkoxy, $C_3$-$C_6$cycloalkoxy; or $R_5$ is selected from a (=O), (=S), (=NH) or (=N(OH)) group;
(16) for a compound of formula (Ia) or (Ib), $R_5$ is amino, halogen, hydroxy, $C_1$-$C_3$alkyl, halogen-$C_1$-$C_3$-alkyl, hydroxy-$C_1$-$C_3$-alkyl, $C_3$-$C_6$cycloalkyl, $C_1$-$C_3$alkoxy, halogen-$C_1$-$C_3$-alkoxy, $C_3$-$C_6$cycloalkoxy; or $R_5$ is selected from a (=O), (=S), (=NH) or (=N(OH)) group;
(17) $R_5$ is halogen, hydroxy, $C_1$-$C_3$alkyl, $C_1$-$C_3$alkoxy;
(18) $R_5$ is halogen;
(19) $R_5$ is fluoro;
(20) $R_5$ is hydroxy;

(21) $R_5$ is methoxy;
(22) $R_5$ is ethoxy;
(23) $R_5$ is isopropyloxy;
(24) for a compound of formula (I), $R_6$ is hydrogen, amino, halogen, hydroxy, $C_1$-$C_3$alkyl, halogen-$C_1$-$C_3$-alkyl, $C_3$-$C_6$cycloalkyl, $C_1$-$C_3$alkoxy, halogen-$C_1$-$C_3$-alkoxy or $C_3$-$C_6$cycloalkoxy; and
$R_7$ is hydrogen, halogen, or halogen-$C_1$-$C_3$-alkyl or
$R_6$ and $R_7$ together with the carbon to which they are attached form a —C(=O)— or —C(=S)— group;
(25) for a compound of formula (Ic) and (Id), $R_6$ is amino, halogen, hydroxy, $C_1$-$C_3$alkyl, halogen-$C_1$-$C_3$-alkyl, $C_3$-$C_6$cycloalkyl, $C_1$-$C_3$alkoxy, halogen-$C_1$-$C_3$-alkoxy or $C_3$-$C_6$cycloalkoxy;
(26) $R_6$ is halogen or hydroxy; and
$R_7$ is hydrogen, halogen, halogen-$C_1$-$C_3$-alkyl or
$R_6$ and $R_7$ together with the carbon to which they are attached form a —C(=O)— group;
(27) $R_6$ is halogen or hydroxy;
(28) $R_6$ is halogen;
(29) $R_6$ is fluoro;
(30) $R_6$ is hydroxy;
(31) $R_7$ is hydrogen, halogen or halogen-$C_1$-$C_3$-alkyl;
(32) $R_7$ is hydrogen;
(33) $R_7$ is halogen;
(34) $R_7$ is fluoro;
(35) $R_7$ is trifluoromethyl.

The skilled person would understand that the embodiments (1) to (35) may be used independently, collectively or in any combination or sub-combination to limit the scope of the invention as described hereinbefore in relation to compounds of formula (I), (Ia), (Ib), (Ic) or (Id), as appropriate.

In one embodiment, the invention provides a compound of formula (I) in free form or in a pharmaceutically acceptable salt form, wherein
$R_1$ is $C_1$-$C_3$alkyl;
$R_2$ is halogen;
$R_3$ is cyano;
$R_4$ is selected from amino, halogen, hydroxy, $C_1$-$C_3$alkyl, halogen-$C_1$-$C_3$alkyl, hydroxy-$C_1$-$C_3$alkyl, $C_3$-$C_6$cycloalkyl, $C_1$-$C_3$alkoxy, halogen-$C_1$-$C_3$alkoxy, $C_1$-$C_3$alkoxy-$C_1$-$C_3$alkoxy, $C_3$-$C_6$cycloalkyl-$C_1$-$C_3$alkoxy, $C_3$-$C_6$cycloalkoxy; or $R_4$ is selected from a (=O), (=S) or (=N($R_8$)) group;
$R_5$ is selected from hydrogen, amino, halogen, hydroxy, $C_1$-$C_3$alkyl, halogen-$C_1$-$C_3$alkyl, hydroxy-$C_1$-$C_3$alkyl, $C_3$-$C_6$cycloalkyl, $C_1$-$C_3$alkoxy, halogen-$C_1$-$C_3$alkoxy, $C_3$-$C_6$cycloalkoxy; or $R_5$ is selected from a (=O), (=S) or (=N($R'_8$)) group;
$R_6$ is selected from hydrogen, halogen, hydroxy, $C_1$-$C_3$alkyl, halogen-$C_1$-$C_3$alkyl, $C_1$-$C_3$alkoxy, halogen-$C_1$-$C_3$alkoxy; and
$R_7$ is selected from hydrogen, halogen or halogen-$C_1$-$C_3$-alkyl, or
$R_6$ and $R_7$ together with the carbon to which they are attached form a —C(=O)— or —C(=S)— group;
$R_8$ and $R'_8$ are independently selected from hydrogen or hydroxy;
provided $R_5$, $R_6$ and $R_7$ are not all hydrogen.

In one embodiment, the invention relates to a compound of formula (I) in free form or in pharmaceutically acceptable salt form wherein
$R_1$ is $C_1$-$C_3$alkyl;
$R_2$ is halogen;
$R_3$ is cyano;
$R_4$ is selected from hydroxy, $C_1$-$C_3$alkyl, halogen-$C_1$-$C_3$alkyl, $C_1$-$C_3$alkoxy, halogen-$C_1$-$C_3$alkoxy, or $R_4$ is selected from a (=O), (=S) or (=N($R_8$)) group;
$R_5$ is selected from hydrogen, halogen, hydroxy, $C_1$-$C_3$alkyl, halogen-$C_1$-$C_3$alkyl, $C_1$-$C_3$alkoxy, halogen-$C_1$-$C_3$alkoxy;
$R_6$ is selected from hydrogen, halogen, hydroxy, $C_1$-$C_3$alkyl, halogen-$C_1$-$C_3$alkyl, $C_1$-$C_3$alkoxy, halogen-$C_1$-$C_3$alkoxy, and
$R_7$ is selected from hydrogen, halogen or halogen-$C_1$-$C_3$-alkyl or
$R_6$ and $R_7$ together with the carbon to which they are attached form a —C(=O)— group;
$R_8$ is hydrogen or hydroxy;
provided $R_5$, $R_6$ and $R_7$ are not all hydrogen.

In one embodiment, the invention relates to a compound of formula (I) in free form or in pharmaceutically acceptable salt form wherein
$R_1$ is $C_1$-$C_3$alkyl;
$R_2$ is halogen;
$R_3$ is cyano;
$R_4$ is selected from hydroxy, $C_1$-$C_3$alkyl, halogen-$C_1$-$C_3$alkyl, $C_1$-$C_3$alkoxy, halogen-$C_1$-$C_3$alkoxy;
$R_5$ is selected from halogen, hydroxy, $C_1$-$C_3$alkyl, halogen-$C_1$-$C_3$alkyl, $C_1$-$C_3$alkoxy, halogen-$C_1$-$C_3$alkoxy;
$R_6$ and $R_7$ are hydrogen.

In one embodiment, the invention relates to a compound of formula (I) in free form or in pharmaceutically acceptable salt form wherein
$R_1$ is $C_1$-$C_3$alkyl;
$R_2$ is halogen;
$R_3$ is cyano;
$R_4$ is selected from hydroxy, $C_1$-$C_3$alkyl, $C_1$-$C_3$alkoxy, halogen-$C_1$-$C_3$alkoxy;
$R_5$ is selected from halogen, hydroxy, $C_1$-$C_3$alkyl, halogen-$C_1$-$C_3$alkyl, $C_1$-$C_3$alkoxy, halogen-$C_1$-$C_3$alkoxy;
$R_6$ and $R_7$ are hydrogen.

In one embodiment, the invention relates to a compound of formula (I) in free form or in pharmaceutically acceptable salt form wherein
$R_1$ is methyl;
$R_2$ is chloro;
$R_3$ is cyano;
$R_4$ is $C_1$-$C_3$alkoxy or halogen-$C_1$-$C_3$alkoxy;
$R_5$ is selected from halogen or hydroxy;
$R_6$ and $R_7$ are hydrogen.

In one embodiment, the invention relates to a compound of formula (I) in free form or in pharmaceutically acceptable salt form wherein
$R_1$ is methyl;
$R_2$ is chloro;
$R_3$ is cyano;
$R_4$ is methoxy;
$R_5$ is selected from fluoro or hydroxy;
$R_6$ and $R_7$ are hydrogen.

In one embodiment, the invention relates to a compound of formula (I) in free form or in pharmaceutically acceptable salt form wherein
$R_1$ is $C_1$-$C_3$alkyl;
$R_2$ is halogen;
$R_3$ is cyano;
$R_4$ is selected from hydroxy, $C_1$-$C_3$alkyl, halogen-$C_1$-$C_3$alkyl, $C_1$-$C_3$alkoxy, halogen-$C_1$-$C_3$alkoxy;
$R_5$ is hydrogen;
$R_6$ is selected from halogen, hydroxy, $C_1$-$C_3$alkyl, halogen-$C_1$-$C_3$alkyl, $C_1$-$C_3$alkoxy, halogen-$C_1$-$C_3$alkoxy, and $R_7$ is selected from hydrogen, halogen or halogen-$C_1$-$C_3$-alkyl or $R_6$ and $R_7$ together with the carbon to which they are attached form a —C(=O)— group.

In one embodiment, the invention relates to a compound of formula (I) in free form or in pharmaceutically acceptable salt form wherein
  $R_1$ is $C_1$-$C_3$alkyl;
  $R_2$ is halogen;
  $R_3$ is cyano;
  $R_4$ is selected from hydroxy, $C_1$-$C_3$alkyl, $C_1$-$C_3$alkoxy;
  $R_5$ is hydrogen;
  $R_6$ is selected from halogen, hydroxy, $C_1$-$C_3$alkyl, halogen-$C_1$-$C_3$alkyl, $C_1$-$C_3$alkoxy, halogen-$C_1$-$C_3$alkoxy, and
  $R_7$ is selected from hydrogen, halogen or halogen-$C_1$-$C_3$-alkyl or
  $R_6$ and $R_7$ together with the carbon to which they are attached form a —C(=O)— group.

In one embodiment, the invention relates to a compound of formula (I) in free form or in pharmaceutically acceptable salt form wherein
  $R_1$ is $C_1$-$C_3$alkyl;
  $R_2$ is halogen;
  $R_3$ is cyano;
  $R_4$ is selected from hydroxy, $C_1$-$C_3$alkyl, $C_1$-$C_3$alkoxy;
  $R_5$ is hydrogen;
  $R_6$ and $R_7$ together with the carbon to which they are attached form a —C(=O)— group.

In one embodiment, the invention relates to a compound of formula (I) in free form or in pharmaceutically acceptable salt form wherein
  $R_1$ is $C_1$-$C_3$alkyl;
  $R_2$ is halogen;
  $R_3$ is cyano;
  $R_4$ is selected from hydroxy, $C_1$-$C_3$alkyl, $C_1$-$C_3$alkoxy;
  $R_5$ is hydrogen;
  $R_6$ is selected from halogen, hydroxy, $C_1$-$C_3$alkyl;
  $R_7$ is selected from hydrogen, halogen or halogen-$C_1$-$C_3$-alkyl.

In one embodiment, the invention relates to a compound of formula (I) in free form or in pharmaceutically acceptable salt form wherein
  $R_1$ is methyl;
  $R_2$ is chloro;
  $R_3$ is cyano;
  $R_4$ is selected from hydroxy, methoxy or ethoxy;
  $R_5$ is hydrogen;
  $R_6$ is selected from halogen, hydroxy, $C_1$-$C_3$alkyl;
  $R_7$ is hydrogen or halogen.

In one embodiment, the invention relates to a compound of formula (Ia) or (Ib) in free form or in pharmaceutically acceptable salt form wherein
  $R_1$ is $C_1$-$C_3$alkyl;
  $R_2$ is halogen;
  $R_3$ is cyano;
  $R_4$ is selected from hydroxy, $C_1$-$C_3$alkyl, halogen-$C_1$-$C_3$alkyl, $C_1$-$C_3$alkoxy, halogen-$C_1$-$C_3$alkoxy;
  $R_5$ is selected from halogen, hydroxy, $C_1$-$C_3$alkyl, halogen-$C_1$-$C_3$alkyl, $C_1$-$C_3$alkoxy, halogen-$C_1$-$C_3$alkoxy.

In one embodiment, the invention relates to a compound of formula (Ia) or (Ib) in free form or in pharmaceutically acceptable salt form wherein
  $R_1$ is $C_1$-$C_3$alkyl;
  $R_2$ is halogen;
  $R_3$ is cyano;
  $R_4$ is selected from hydroxy, $C_1$-$C_3$alkyl, $C_1$-$C_3$alkoxy;
  $R_5$ is selected from halogen, hydroxy, $C_1$-$C_3$alkyl, halogen-$C_1$-$C_3$alkyl, $C_1$-$C_3$alkoxy, halogen-$C_1$-$C_3$alkoxy.

In one embodiment, the invention relates to a compound of formula (Ia) or (Ib) in free form or in pharmaceutically acceptable salt form wherein
  $R_1$ is methyl;
  $R_2$ is chloro;
  $R_3$ is cyano;
  $R_4$ is selected from hydroxy, $C_1$-$C_3$alkyl, $C_1$-$C_3$alkoxy;
  $R_5$ is selected from halogen, hydroxy, $C_1$-$C_3$alkyl, halogen-$C_1$-$C_3$alkyl, $C_1$-$C_3$alkoxy, halogen-$C_1$-$C_3$alkoxy.

In one embodiment, the invention relates to a compound of formula (Ia) or (Ib) in free form or in pharmaceutically acceptable salt form wherein
  $R_1$ is methyl;
  $R_2$ is chloro;
  $R_3$ is cyano;
  $R_4$ is $C_1$-$C_3$alkoxy;
  $R_5$ is selected from halogen or hydroxy.

In one embodiment, the invention relates to a compound of formula (Ia) or (Ib) in free form or in pharmaceutically acceptable salt form wherein
  $R_1$ is methyl;
  $R_2$ is chloro;
  $R_3$ is cyano;
  $R_4$ is methoxy;
  $R_5$ is selected from fluoro or hydroxy.

In one embodiment, the invention relates to a compound of formula (Ic) or (Id) in free form or in pharmaceutically acceptable salt form wherein
  $R_1$ is $C_1$-$C_3$alkyl;
  $R_2$ is halogen;
  $R_3$ is cyano;
  $R_4$ is selected from hydroxy, $C_1$-$C_3$alkyl, halogen-$C_1$-$C_3$alkyl, $C_1$-$C_3$alkoxy, halogen-$C_1$-$C_3$alkoxy;
  $R_6$ is selected from halogen, hydroxy, $C_1$-$C_3$alkyl, halogen-$C_1$-$C_3$alkyl, $C_1$-$C_3$alkoxy, halogen$C_1$-$C_3$alkoxy.

In one embodiment, the invention relates to a compound of formula (Ic) or (Id) in free form or in pharmaceutically acceptable salt form wherein
  $R_1$ is $C_1$-$C_3$alkyl;
  $R_2$ is halogen;
  $R_3$ is cyano;
  $R_4$ is selected from hydroxy, $C_1$-$C_3$alkyl, $C_1$-$C_3$alkoxy;
  $R_6$ is selected from halogen, hydroxy, $C_1$-$C_3$alkyl, halogen-$C_1$-$C_3$alkyl, $C_1$-$C_3$alkoxy, halogen-$C_1$-$C_3$alkoxy.

In one embodiment, the invention relates to a compound of formula (Ic) or (Id) in free form or in pharmaceutically acceptable salt form wherein
  $R_1$ is methyl;
  $R_2$ is chloro;
  $R_3$ is cyano;
  $R_4$ is $C_1$-$C_3$alkoxy;
  $R_6$ is halogen.

In one embodiment, the invention provides a compound which is selected from
2-chloro-4-(4-hydroxy-3-methoxy-3a,4,5,6-tetrahydro-3H-pyrrolo[1,2-b]pyrazol-2-yl)-3-methylbenzonitrile;
2-chloro-4-(3,4-dihydroxy-3a,4,5,6-tetrahydro-3H-pyrrolo[1,2-b]pyrazol-2-yl)-3-methylbenzonitrile;
2-chloro-4-(3-ethoxy-4-hydroxy-3a,4,5,6-tetrahydro-3H-pyrrolo[1,2-b]pyrazol-2-yl)-3-methylbenzonitrile;
2-chloro-4-(4-hydroxy-3-isopropoxy-3a,4,5,6-tetrahydro-3H-pyrrolo[1,2-b]pyrazol-2-yl)-3-methylbenzonitrile;
2-chloro-4-(5-hydroxy-3-methoxy-3a,4,5,6-tetrahydro-3H-pyrrolo[1,2-b]pyrazol-2-yl)-3-methylbenzonitrile;

2-chloro-4-(3-methoxy-5-oxo-3a,4,5,6-tetrahydro-3H-pyrrolo[1,2-b]pyrazol-2-yl)-3-methylbenzonitrile;
2-chloro-4-(3,5-dihydroxy-3a,4,5,6-tetrahydro-3H-pyrrolo[1,2-b]pyrazol-2-yl)-3-methylbenzonitrile;
2-chloro-4-(5-hydroxy-3-methoxy-5-(trifluoromethyl)-3a,4,5,6-tetrahydro-3H-pyrrolo[1,2-b]pyrazol-2-yl)-3-methylbenzonitrile;
2-chloro-4-(4-fluoro-3-methoxy-3a,4,5,6-tetrahydro-3H-pyrrolo[1,2-b]pyrazol-2-yl)-3-methylbenzonitrile;
2-chloro-4-(5-fluoro-3-methoxy-3a,4,5,6-tetrahydro-3H-pyrrolo[1,2-b]pyrazol-2-yl)-3-methylbenzonitrile;
2-chloro-4-(5,5-difluoro-3-methoxy-3a,4,5,6-tetrahydro-3H-pyrrolo[1,2-b]pyrazol-2-yl)-3-methylbenzonitrile;
2-chloro-4-(3-(2-fluoroethoxy)-4-hydroxy-3a,4,5,6-tetrahydro-3H-pyrrolo[1,2-b]pyrazol-2-yl)-3-methylbenzonitrile;
2-chloro-4-(3-(cyclopropylmethoxy)-4-hydroxy-3a,4,5,6-tetrahydro-3H-pyrrolo[1,2-b]pyrazol-2-yl)-3-methylbenzonitrile;
2-chloro-4-(5-iodo-3-methoxy-3a,4,5,6-tetrahydro-3H-pyrrolo[1,2-b]pyrazol-2-yl)-3-methylbenzonitrile;
2-chloro-4-(3,4-dimethoxy-3a,4,5,6-tetrahydro-3H-pyrrolo[1,2-b]pyrazol-2-yl)-3-methylbenzonitrile;
2-chloro-4-(4-hydroxy-3-(2-methoxyethoxy)-3a,4,5,6-tetrahydro-3H-pyrrolo[1,2-b]pyrazol-2-yl)-3-methylbenzonitrile;
2-chloro-4-(4-fluoro-3-(2-methoxyethoxy)-3a,4,5,6-tetrahydro-3H-pyrrolo[1,2-b]pyrazol-2-yl)-3-methylbenzonitrile;
2-chloro-4-(4-fluoro-3-(2-fluoroethoxy)-3a,4,5,6-tetrahydro-3H-pyrrolo[1,2-b]pyrazol-2-yl)-3-methylbenzonitrile and
2-chloro-4-(5,5-difluoro-3-(2-methoxyethoxy)-3a,4,5,6-tetrahydro-3H-pyrrolo[1,2-b]pyrazol-2-yl)-3-methylbenzonitrile
in free form or in pharmaceutically acceptable salt form.

In one embodiment, the invention provides a compound which is selected from
2-chloro-4-((3S,3aS,4S)-4-hydroxy-3-methoxy-3a,4,5,6-tetrahydro-3H-pyrrolo[1,2-b]pyrazol-2-yl)-3-methylbenzonitrile;
2-chloro-4-((3S,3aS,4R)-4-hydroxy-3-methoxy-3a,4,5,6-tetrahydro-3H-pyrrolo[1,2-b]pyrazol-2-yl)-3-methylbenzonitrile;
2-chloro-4-((3S,3aS,4S)-3,4-dihydroxy-3a,4,5,6-tetrahydro-3H-pyrrolo[1,2-b]pyrazol-2-yl)-3-methylbenzonitrile;
2-chloro-4-((3S,3aS,4R)-3,4-dihydroxy-3a,4,5,6-tetrahydro-3H-pyrrolo[1,2-b]pyrazol-2-yl)-3-methylbenzonitrile;
2-chloro-4-((3S,3aS,4S)-3-ethoxy-4-hydroxy-3a,4,5,6-tetrahydro-3H-pyrrolo[1,2-b]pyrazol-2-yl)-3-methylbenzonitrile;
2-chloro-4-((3S,3aS,4R)-3-ethoxy-4-hydroxy-3a,4,5,6-tetrahydro-3H-pyrrolo[1,2-b]pyrazol-2-yl)-3-methylbenzonitrile;
2-chloro-4-((3S,3aS,4S)-4-hydroxy-3-isopropoxy-3a,4,5,6-tetrahydro-3H-pyrrolo[1,2-b]pyrazol-2-yl)-3-methylbenzonitrile;
2-chloro-4-((3S,3aS,4R)-4-hydroxy-3-isopropoxy-3a,4,5,6-tetrahydro-3H-pyrrolo[1,2-b]pyrazol-2-yl)-3-methylbenzonitrile;
2-chloro-4-((3S,3aS,5R)-5-hydroxy-3-methoxy-3a,4,5,6-tetrahydro-3H-pyrrolo[1,2-b]pyrazol-2-yl)-3-methylbenzonitrile;
2-chloro-4-((3S,3aS)-3-methoxy-5-oxo-3a,4,5,6-tetrahydro-3H-pyrrolo[1,2-b]pyrazol-2-yl)-3-methylbenzonitrile;
2-chloro-4-((3S,3aS,5R)-3,5-dihydroxy-3a,4,5,6-tetrahydro-3H-pyrrolo[1,2-b]pyrazol-2-yl)-3-methylbenzonitrile;
2-chloro-4-((3S,3aS,5S)-3,5-dihydroxy-3a,4,5,6-tetrahydro-3H-pyrrolo[1,2-b]pyrazol-2-yl)-3-methylbenzonitrile;
2-chloro-4-((3S,3aS,5S)-5-hydroxy-3-methoxy-5-(trifluoromethyl)-3a,4,5,6-tetrahydro-3H-pyrrolo[1,2-b]pyrazol-2-yl)-3-methylbenzonitrile;
2-chloro-4-((3S,3aS,5R)-5-hydroxy-3-methoxy-5-(trifluoromethyl)-3a,4,5,6-tetrahydro-3H-pyrrolo[1,2-b]pyrazol-2-yl)-3-methylbenzonitrile;
2-chloro-4-((3S,3aR,4R)-4-fluoro-3-methoxy-3a,4,5,6-tetrahydro-3H-pyrrolo[1,2-b]pyrazol-2-yl)-3-methylbenzonitrile;
2-chloro-4-((3S,3aR,4S)-4-fluoro-3-methoxy-3a,4,5,6-tetrahydro-3H-pyrrolo[1,2-b]pyrazol-2-yl)-3-methylbenzonitrile;
2-chloro-4-((3S,3aS,5S)-5-fluoro-3-methoxy-3a,4,5,6-tetrahydro-3H-pyrrolo[1,2-b]pyrazol-2-yl)-3-methylbenzonitrile;
2-chloro-4-((3S,3aS,5R)-5-fluoro-3-methoxy-3a,4,5,6-tetrahydro-3H-pyrrolo[1,2-b]pyrazol-2-yl)-3-methylbenzonitrile;
2-chloro-4-((3S,3aS)-5,5-difluoro-3-methoxy-3a,4,5,6-tetrahydro-3H-pyrrolo[1,2-b]pyrazol-2-yl)-3-methylbenzonitrile;
2-chloro-4-((3S,3aS,4S)-3-(2-fluoroethoxy)-4-hydroxy-3a,4,5,6-tetrahydro-3H-pyrrolo[1,2-b]pyrazol-2-yl)-3-methylbenzonitrile;
2-chloro-4-((3S,3aS,4R)-3-(2-fluoroethoxy)-4-hydroxy-3a,4,5,6-tetrahydro-3H-pyrrolo[1,2-b]pyrazol-2-yl)-3-methylbenzonitrile;
2-chloro-4-((3S,3aS,4S)-3-(cyclopropylmethoxy)-4-hydroxy-3a,4,5,6-tetrahydro-3H-pyrrolo[1,2-b]pyrazol-2-yl)-3-methylbenzonitrile;
2-chloro-4-((3S,3aS,4R)-3-(cyclopropylmethoxy)-4-hydroxy-3a,4,5,6-tetrahydro-3H-pyrrolo[1,2-b]pyrazol-2-yl)-3-methylbenzonitrile;
2-chloro-4-((3S,3aS,5S)-5-iodo-3-methoxy-3a,4,5,6-tetrahydro-3H-pyrrolo[1,2-b]pyrazol-2-yl)-3-methylbenzonitrile;
2-chloro-4-((3S,3aS,5R)-5-iodo-3-methoxy-3a,4,5,6-tetrahydro-3H-pyrrolo[1,2-b]pyrazol-2-yl)-3-methylbenzonitrile;
2-chloro-4-((3S,3aS,4S)-3,4-dimethoxy-3a,4,5,6-tetrahydro-3H-pyrrolo[1,2-b]pyrazol-2-yl)-3-methylbenzonitrile;
2-chloro-4-((3S,3aS,4R)-3,4-dimethoxy-3a,4,5,6-tetrahydro-3H-pyrrolo[1,2-b]pyrazol-2-yl)-3-methylbenzonitrile;
2-chloro-4-((3S,3aS,4S)-4-hydroxy-3-(2-methoxyethoxy)-3a,4,5,6-tetrahydro-3H-pyrrolo[1,2-b]pyrazol-2-yl)-3-methylbenzonitrile;
2-chloro-4-((3S,3aS,4R)-4-hydroxy-3-(2-methoxyethoxy)-3a,4,5,6-tetrahydro-3H-pyrrolo[1,2-b]pyrazol-2-yl)-3-methylbenzonitrile;
2-chloro-4-((3S,3aR,4R)-4-fluoro-3-(2-methoxyethoxy)-3a,4,5,6-tetrahydro-3H-pyrrolo[1,2-b]pyrazol-2-yl)-3-methylbenzonitrile;
2-chloro-4-((3S,3aR,4S)-4-fluoro-3-(2-methoxyethoxy)-3a,4,5,6-tetrahydro-3H-pyrrolo[1,2-b]pyrazol-2-yl)-3-methylbenzonitrile;
2-chloro-4-((3S,3aR,4R)-4-fluoro-3-(2-fluoroethoxy)-3a,4,5,6-tetrahydro-3H-pyrrolo[1,2-b]pyrazol-2-yl)-3-methylbenzonitrile;

2-chloro-4-((3S,3aR,4S)-4-fluoro-3-(2-fluoroethoxy)-3a,4,5,6-tetrahydro-3H-pyrrolo[1,2-b]pyrazol-2-yl)-3-methylbenzonitrile and 2-chloro-4-((3S,3aS)-5,5-difluoro-3-(2-methoxyethoxy)-3a,4,5,6-tetrahydro-3H-pyrrolo[1,2-b]pyrazol-2-yl)-3-methylbenzonitrile in free form or in pharmaceutically acceptable salt form.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diastereomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Pharmaceutically acceptable solvates in accordance with the invention include those wherein the solvent of crystallization may be isotopically substituted, e.g. $D_2O$, EtOD, or $CH_3CO_2D$.

Compounds of the invention, i.e. compounds of formula (I), (Ia), (Ib), (Ic), or (Id) that contain groups capable of acting as donors and/or acceptors for hydrogen bonds may be capable of forming co-crystals with suitable co-crystal formers. These co-crystals may be prepared from compounds of formula (I), (Ia), (Ib), (Ic), or (Id) by known co-crystal forming procedures. Such procedures include grinding, heating, co-subliming, co-melting, or contacting in solution compounds of formula (I), (Ia), (Ib), (Ic), or (Id) with the co-crystal former under crystallization conditions and isolating co-crystals thereby formed. Suitable co-crystal formers include those described in WO 2004/078163. Hence the invention further provides co-crystals comprising a compound of formula (I), (Ia), (Ib), (Ic), or (Id).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by androgen receptor, or (ii) associated with androgen receptor activity, or (iii) characterized by activity (normal or abnormal) of androgen receptor; or (2) modulating the activity of androgen receptor; or (3) modulating the expression of androgen receptor. In another non-limiting embodiment, the term "a therapeutically effective amount" refers to the amount of the compound of the present invention that, when administered to a cell, or a tissue, or a non-cellular biological material, or a medium, is effective to at least partially modulate the activity of androgen receptor; or at least partially modulate the expression of androgen receptor. The meaning of the term "a therapeutically effective amount" as illustrated in the above embodiment for the androgen receptor also applies by the same means to any other relevant proteins/peptides/enzymes, such as sex hormone-binding globulin (SHBG), or the putative testosterone-binding G-protein coupled receptor (GPRC6A), and the like.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "modulate" refers to the capacity to either enhance (e.g. "agonist" activity) or inhibit (e.g. "antagonist" activity) a functional property of biological activity or process (e.g. enzyme activity or receptor binding); such enhancement or inhibition may be contingent on the occurrence of a specific event, such as regulation of a signal transduction pathway, and/or may be manifest only in particular cell types.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Typically, the compounds of formula (I), (Ia), (Ib), (Ic) or (Id) in free form or in pharmaceutically acceptable salt form can be prepared according to Scheme 1 provided infra.

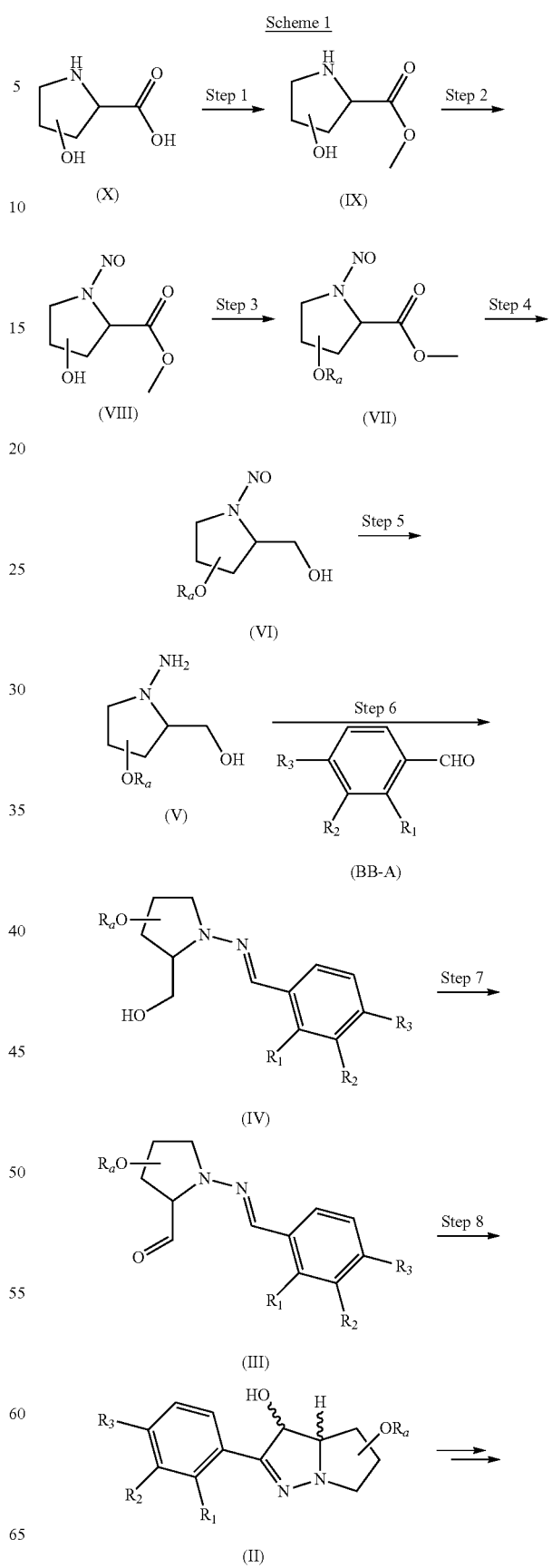

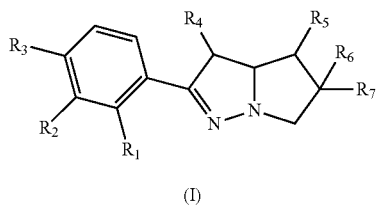

(I)

The process steps are described in more detail below:

Step 1: A compound of formula (IX) may be obtained by reacting a compound of formula (X) in the presence of a suitable Lewis Acid, e.g. boron trifluoride, and a suitable solvent, e.g. methanol.

Step 2: A compound of formula (VIII) may be obtained by reacting a compound of formula (IX) in the presence of a suitable nitrosylation agent, e.g. sodium nitrite, a suitable acid, e.g. acetic acid, and a suitable solvent, e.g. water.

Step 3: A compound of formula (VII) in which $R_a$ represents a protecting group may be obtained by reacting a compound of formula (VIII) with a suitable protecting agent, e.g. tert-butyldimethylsilyl chloride, in the presence of a suitable base, e.g. imidazole.

Step 4: A compound of formula (VI) in which $R_a$ represents a protecting group may be obtained by reacting a compound of formula (VII) with a suitable reducing agent, e.g. lithium triethyl borohydride, in a suitable solvent, e.g. tetrahydrofuran.

Step 5: A compound of formula (V) in which $R_a$ represents a protecting group may be obtained by reacting a compound of formula (VI) with a suitable reducing agent, e.g. zinc, in the presence of a suitable acid, e.g. ammonium chloride, and a suitable solvent, e.g. methanol.

Step 6: A compound of formula (IV) in which $R_a$ represents a protecting group and $R_1$, $R_2$ and $R_3$ are as defined under formula (I) may be obtained by reacting a compound of formula (V) with a compound of formula (BB-A) wherein $R_1$, $R_2$ and $R_3$ are as defined under formula (I), in the presence of a suitable acid, e.g. acetic acid.

Step 7: A compound of formula (III) in which $R_a$ represents a protecting group and $R_1$, $R_2$ and $R_3$ are as defined under formula (I) may be obtained by reacting a compound of formula (IV) with a suitable oxidising agent, e.g. oxalyl chloride, in a suitable solvent, e.g. dichloromethane.

Step 8: A compound of formula (II) in which $R_a$ represents a protecting group and $R_1$, $R_2$ and $R_3$ are as defined under formula (I) may be obtained by cyclisation of a compound of formula (III) using a suitable Lewis acid, e.g. boron trifluoride, in a suitable solvent, e.g. dichloromethane.

Compounds of formula I may be obtainable from compounds of formula (II) prepared as described in Scheme 1—by further reduction, oxidation and/or other functionalization of resulting compounds and/or by cleavage of any protecting group(s) optionally introduced, and by recovering the so obtainable compounds of the formula I in free form or in pharmaceutically acceptable salt form.

In a further aspect, the invention relates to a process for the preparation of a compound of formula (I), in free from or in pharmaceutically acceptable salt form, comprising the steps of:

a) the ring closure of a compound of the formula (III) in free form or in salt form in the presence of a suitable solvent and a suitable Lewis acid to give a compound of formula (II);

b) the optional reduction, oxidation and/or other functionalization of the resulting compound of formula (II);

c) the cleavage of any protecting group(s) optionally present;

d) the recovery of the so obtainable compound of formula (I) in free form or in pharmaceutically acceptable salt form.

Examples of suitable solvents for step a) include dichloromethane (DCM), ether, tetrahydrofuran (THF).

Examples of suitable Lewis acids for step a) include boron trifluoride, titanium tetrachloride.

Examples of typical protecting groups include t-butyldimethylsilyl (TBDMS), methoxymethyl (MOM), tetrahydropyranyl (THP), t-butyldiphenylsilyl (TBDPS).

The reactions can be effected according to conventional methods, for example as described in the Examples.

The work-up of the reaction mixtures and the purification of the compounds thus obtainable may be carried out in accordance with known procedures.

Acid addition salts may be produced from the free bases in known manner, and vice-versa.

Compounds of the formula I can also be prepared by further conventional processes, for example as described in the Examples, which processes are further aspects of the invention.

The starting materials used are known or may be prepared according to conventional procedures starting from known compounds, for example as described in the Examples.

The invention further includes any variant of the present process, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

In a further aspect, the invention relates to a compound of formula (III) in free form or in pharmaceutically acceptable salt form

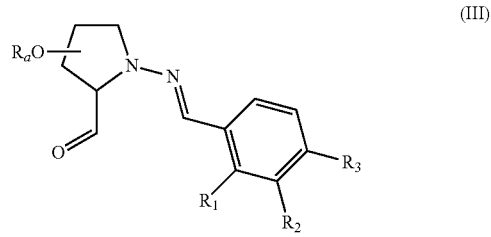

(III)

wherein $R_1$, $R_2$ and $R_3$ are as defined in relation to formula (I) and wherein $R_a$ is a protecting group.

In another aspect, the invention relates to a compound of formula (III') or (III") in free form or in pharmaceutically acceptable salt form

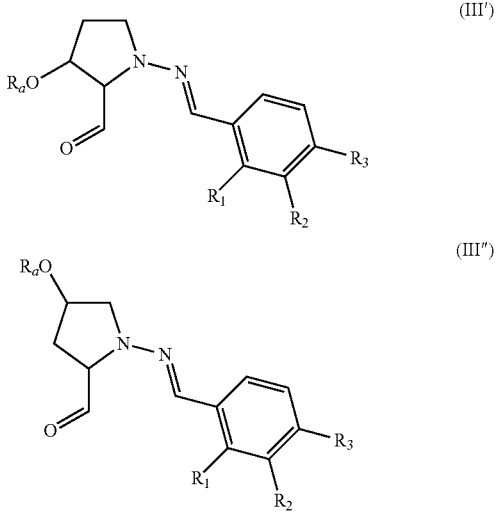

wherein $R_1$, $R_2$ and $R_3$ are as defined in relation to formula (I) and wherein $R_a$ is a protecting group.

In the context of the compounds of formula (III), (III') and (III"), suitable $R_a$ protecting groups include t-butyldimethylsilyl (TBDMS), methoxymethyl (MOM), tetrahydropyranyl (THP), t-butyldiphenylsilyl (TBDPS).

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with
 a) diluents, e.g., lactose, dextrose, sucrose, mannitol, sorbitol, cellulose and/or glycine;
 b) lubricants, e.g., silica, talcum, stearic acid, its magnesium or calcium salt and/or polyethyleneglycol; for tablets also
 c) binders, e.g., magnesium aluminum silicate, starch paste, gelatin, tragacanth, methylcellulose, sodium carboxymethylcellulose and/or polyvinylpyrrolidone; if desired
 d) disintegrants, e.g., starches, agar, alginic acid or its sodium salt, or effervescent mixtures; and/or
 e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with or without a suitable permeation enhancer (including without limitation volatile or nonvolatile solvents) that improves the diffusion and solubility of the compound in the skin, other functional and non functional excipients (including without limiting, humectants, stabilizers, oils, surfactants, polymers, preservatives, antioxidants, moisturizers, emollients, solubilizers, penetration enhancers, skin protectants) and carriers suitable for transdermal delivery. The transdermal pharmaceutical compositions of the present invention can be made up in a semi-solid form (including without limitation gel, creams, ointments), solutions (including combination of several volatile and non volatile solvents and other pharmaceutical excipients) or solid (including without limitation reservoir patches, matrix patches, "patchless" formulations) comprising a backing member, a reservoir containing the compound optionally with carriers, optionally a rate controlling barrier to deliver the compound of the skin of the host at a controlled and predetermined rate over a prolonged period of time, and means to secure the device to the skin.

Moreover, administration through the skin by means of devices with or without the help of energy (including without limitation microneedle, iotophoresis, sonophoresis, thermal ablation) can be envisaged for delivery of the compound.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be desirable.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of the invention in free form or in salt form, exhibit valuable pharmacological properties, e.g. androgen receptor modulating properties, for example as indicated in in vitro and in vivo tests as provided in the next sections and are therefore indicated for therapy.

Compounds of the invention may be useful in the treatment or prevention of an indication selected from: muscular atrophy; lipodistrophy; long-term critical illness; sarcopenia; frailty or age-related functional decline; reduced muscle strength and function; reduced bone density or growth such as osteoporosis and osteopenia; the catabolic side effects of glucocorticoids; chronic fatigue syndrome; chronic myalgia; bone fracture; acute fatigue syndrome; muscle loss following elective surgery; cachexia; chronic catabolic state; eating disorders; side effects of chemotherapy; wasting secondary to fractures; wasting in connection with chronic obstructive pulmonary disease (COPD), chronic liver disease, AIDS, weightlessness, cancer cachexia, burn and trauma recovery, chronic catabolic state such as coma, eating disorders such as anorexia and chemotherapy; depression; nervousness; irritability; stress; growth retardation; reduced cognitive function; male contraception; hypogonadism; Syndrome X; diabetic complications or obesity.

In particular, compounds of the invention may be useful in the treatment or prevention of muscle wasting diseases, osteoporosis, sarcopenia, frailty, and cancer cachexia.

Thus, as a further embodiment, the present invention provides the use of a compound of formula (I), (Ia), (Ib), (Ic) or (Id) in free from or in pharmaceutically acceptable salt form in therapy. In a further embodiment, the therapy is selected from a disease which may be treated by modulation of androgen receptor. In another embodiment, the disease is selected from the afore-mentioned list, suitably muscle wasting diseases, osteoporosis, sarcopenia, frailty, and cancer cachexia, more suitably cancer cachexia and sarcopenia.

In another embodiment, the invention provides a method of treating a disease which is treated by modulation of androgen receptor comprising administration of a therapeutically acceptable amount of a compound of formula (I), (Ia), (Ib), (Ic) or (Id) in free from or in pharmaceutically acceptable salt form.

In a further embodiment, the disease is selected from the afore-mentioned list, suitably muscle wasting diseases, osteoporosis, sarcopenia, frailty, and cancer cachexia, more suitably cancer cachexia and sarcopenia.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.

Test 1: In Vitro Assay

A suitable assay to determine the ability of a ligand to transcriptionally activate androgen receptor (AR) is carried out using mouse myoblastic C2C12 cells. The assay involves transfecting C2C12 cells with a plasmid containing full-length AR along with an AR response element linked to luciferase (2XIDR17). The luminescence read-out at the end of the assay is measured using Victor 3 and is a direct measure of the transcriptional activity. The assay has been validated using the reference compound, BMS-564929, for which $EC_{50}$ values have been reported in a similar set-up. Other tool compounds that have been used for assay validation are GSK-420A, Andarine, putative Ostarine, and LGD-2226.

Test 2: In Vivo Modified Hershberger Assay

The test article Testosterone Propionate is dissolved using 10% ethanol, 90% corn oil. Ostarine is suspended in 1% CMC, 0.1% Tween-80, water. Compounds of examples 1 and 5 are dissolved in 50% PEG 200 and 50% of saline. Ostarine is administered orally at 1 ml/kg volume. Testosterone Propionate, Compounds of examples 1 and 5 are administered subcutaneously to 14 days prior orchidectomized male rats at 1 ml per kg body weight for a period of 14 days. Each group of 6 rats receives dosages of 0.01, 0.1, 1 and 10 mg/kg. 6 animals each serves as sham control and ORX control and are administered vehicle at 1 ml/kg.

Testosterone Propionate is subcutaneously administered at doses of 0.03, 0.1, 0.3, 1.3 and 10 mg/kg. Ostarine is given orally at doses of 0.001, 0.003, 0.01, 0.03, 0.1, 0.3, 1.3 and 10 mg/kg.

The various investigations like mortality, clinical signs, body weight, food consumption, drug concentration analysis (day 15), clinical pathology and gross pathology parameters are performed on all groups.

The compounds of the invention were tested in at least one of the above-described tests. Specific results for the compounds of the invention are described in Examples 19 and 20.

The compounds of the present invention may be administered either simultaneously with, or before or after, one or more other therapeutic agent. The compounds of the present invention may be administered separately, by the same or different route of administration, or together in the same pharmaceutical composition as the other agents.

In one embodiment, the invention relates to a combination comprising a therapeutically effective amount of a compound of the invention in free form or in pharmaceutically acceptable salt form and one or more therapeutically active co-agents.

In one embodiment, the invention provides a product comprising a compound of the invention in free from or in pharmaceutically acceptable salt form and at least one other therapeutic agent as a combined preparation for simultaneous, separate or sequential use in therapy. In one embodiment, the therapy is the treatment of a disease or condition mediated by androgen receptor modulation. Products provided as a combined preparation include a composition comprising a compound of the invention in free from or in pharmaceutically acceptable salt form and the other therapeutic agent(s) together in the same pharmaceutical composition, or a compound of the invention in free from or in pharmaceutically acceptable salt form and the other therapeutic agent(s) in separate form, e.g. in the form of a kit.

In one embodiment, the invention provides a pharmaceutical composition comprising a compound of the invention in free from or in pharmaceutically acceptable salt form and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of the invention in free from or in pharmaceutically acceptable salt form. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of the invention in free from or in pharmaceutically acceptable salt form for treating a disease or condition mediated by androgen receptor modulation, wherein the medicament is prepared for administration with another therapeutic agent. The invention also provides the use of another therapeutic agent for treating a disease or condition mediated by androgen receptor modulation, wherein the medicament is administered with a compound of the invention.

The invention also provides a compound of the invention in free from or in pharmaceutically acceptable salt form for use in a method of treating a disease or condition mediated by androgen receptor modulation, wherein the compound of the invention is prepared for administration with another therapeutic agent. The invention also provides another therapeutic agent for use in a method of treating a disease or condition mediated by androgen receptor modulation, wherein the other therapeutic agent is prepared for administration with a compound of the invention in free from or in pharmaceutically acceptable salt form. The invention also provides a compound of the invention in free from or in pharmaceutically acceptable salt form for use in a method of treating a disease or condition mediated by androgen receptor modulation, wherein the compound of the invention in free from or in pharmaceutically acceptable salt form is administered with another therapeutic agent. The invention also provides another therapeutic agent for use in a method of treating a disease or condition mediated by androgen receptor modulation, wherein the other therapeutic agent is administered with a compound of the invention in free from or in pharmaceutically acceptable salt form.

The invention also provides the use of a compound of the invention in free from or in pharmaceutically acceptable salt form for treating a disease or condition mediated by androgen receptor modulation, wherein the patient has previously (e.g. within 24 hours) been treated with another therapeutic agent. The invention also provides the use of another therapeutic agent for treating a disease or condition mediated by androgen receptor modulation, wherein the patient has previously (e.g. within 24 hours) been treated with a compound of the invention in free from or in pharmaceutically acceptable salt form.

The following examples are intended to illustrate the invention and are not to be construed as being limitations thereon. Temperatures are given in degrees centrigrade. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

EXAMPLES

Abbreviations

AcOH acetic acid
cm centimeters
CuI copper iodide
d doublet
dd doublet of doublets
DAST diethylaminosulfurtrifluoride
DCM dichloromethane
DIAD diisopropyl azodicarboxylate
DMF N,N-dimethylformamide
DMSO dimethylsulfoxide
ES electron-spray
EtOAc ethyl acetate
EtOH ethanol
g grams
h hour(s)
HCl hydrochloric acid
HPLC high pressure liquid chromatography
IR infrared spectroscopy
LCMS liquid chromatography and mass spectrometry
1M one molar
MeOH methanol
MHz megahertz
MS mass spectrometry
m multiplet
mbar millibar
min minutes
mL milliliter(s)
m/z mass to charge ratio
NaH sodium hydride
NaHCO$_3$ sodium bicarbonate
Na$_2$SO$_4$ sodium sulfate
nM nanomolar
NMR nuclear magnetic resonance
PCC pyridinium chlorochromate
PPh$_3$ triphenylphosphine
ppm parts per million
PPTS pyrididium p-toluenesulfonate
rt room temperature
s singlet
sat saturated
t triplet
TBAF tetrabutyl ammoniumfluoride
TBS t-butyl dimethylsilyl
TBDMS-Cl t-butyl dimethylsilyl chloride
TFA trifluoroacetic acid
THF tetrahydrofuran
TLC thin layer chromatography
μm micrometers
wt weight

Instruments Used

NMR-400 MHz: Varian, Mercury
NMR-500 MHz: Varian, Unity INOVA
ES-MS: Applied Biosystems, API-3000
FT-IR: Shimadzu, IR Prestige 21

EXPERIMENTAL

Building block A1:
2-chloro-4-formyl-3-methylbenzonitrile (BB-A1)

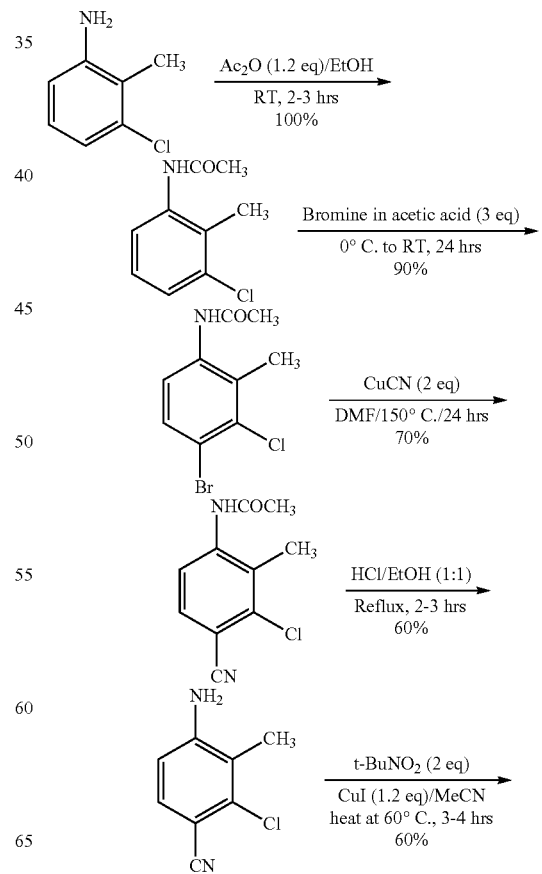

-continued

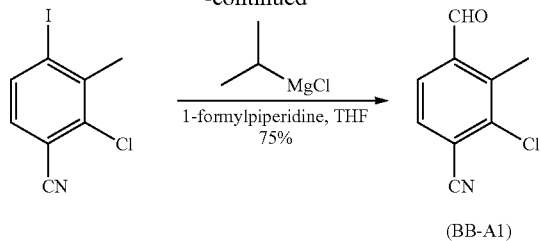

(BB-A1)

a) N-(3-chloro-2-methylphenyl)acetamide

To a solution of 3-chloro-2-methylaniline (27 g, 0.19 mol) in 270 mL of ETOH at rt was added acetic anhydride (22 mL, 0.23 mol), and the solution was stirred at rt for 2 h. The mixture was concentrated under reduced pressure to give 35 g (100%) of the title compound.

$^1$H NMR (400 MHz, DMSO-$d_6$): δ 9.53 (bs, 1H), 7.32-7.25 (m, 2H), 7.19-7.15 (m, 1H), 2.21 (s, 3H), 2.05 (s, 3H); MS (ES): m/z 184.2 (M+1).

b) N-(4-bromo-3-chloro-2-methylphenyl)acetamide

To a suspension of N-(3-chloro-2-methylphenyl)acetamide (35 g, 0.19 mol) in 350 mL of glacial AcOH cooled to 0° C. was added bromine (29.5 mL, 0.57 mol) dropwise. The ice bath was removed and the solution was stirred for 24 h and then poured into ice water with stirring. The solid was then filtered and dried to give the title compound (45 g, 90%) which was used for the next step without any further purification.

$^1$H NMR (400 MHz, DMSO-$d_6$): δ 9.60 (bs, 1H), 7.58 (d, J=8.8 Hz, 1H), 7.30 (d, J=8.7 Hz, 1H), 2.29 (s, 3H), 2.06 (s, 3H); MS (ES): m/z 261.9 (M+1).

c) N-(3-chloro-4-cyano-2-methylphenyl)acetamide

A suspension of N-(4-bromo-3-chloro-2-methylphenyl)acetamide (45 g, 0.17 mol) and copper cyanide (34 g, 0.34 mol) in DMF (450 mL) was heated to 150° C. for 24 h. The suspension was cooled, poured into water with stirring. The solid was filtered and dried to give 25 g (70%) of the title compound which was used for the next step without further purification.

$^1$H NMR (400 MHz, DMSO-$d_6$): δ 9.73 (bs, 1H), 7.78-7.73 (m, 2H), 2.31 (s, 3H), 2.13 (s, 3H); IR (KBr): 3307, 3097, 3014, 2235, 1930, 1674, 1514 cm$^{-1}$; MS (ES): m/z 207 (M−1).

d) 4-amino-2-chloro-3-methylbenzonitrile

A solution of N-(3-chloro-4-cyano-2-methylphenyl)acetamide (25 g, 0.119 mol) in 250 mL of concentrated HCl/EtOH (1:1) was refluxed 2 hrs. The EtOH was concentrated and ethyl acetate was added to the residue and the aqueous layer was neutralized with addition of saturated NaHCO$_3$ solution. The organic layer was separated and dried over Na$_2$SO$_4$ and concentrated to give the crude aniline which was further purified by column chromatography using DCM as a solvent to yield the title compound (11.8 g, 60%).

$^1$H NMR (400 MHz, DMSO-$d_6$): δ 7.37 (d, J=8.4 Hz, 1H), 6.62 (d, J=8.8 Hz, 1H), 6.29 (bs, 2H), 2.13 (s, 3H); IR (KBr): 3487, 3375, 3246, 2652, 2220, 1627, 1597 cm$^{-1}$; MS (ES): m/z 167.1 (M+1).

e) 2-chloro-4-iodo-3-methylbenzonitrile

To a suspension of CuI (16.2 g, 0.085 mol) in acetonitrile (120 mL) under nitrogen at rt was added tert-butylnitrite (16.8 mL, 0.147 mol). The reaction mixture was heated to 65° C. for 1 h and then 4-amino-2-chloro-3-methylbenzonitrile (11.8 g, 0.071 mol) was added and the reaction was heated at 65° C. for 3 h. The reaction was cooled to rt and filtered through a pad of celite. The celite pad was washed with EtOAc. The organic layer was washed with water, dried over Na$_2$SO$_4$, filtered and concentrated to get the crude product which was purified by flash column chromatography using 5% EtOAc in hexane as a solvent to give the title compound. Yield 11.8 g (60%).

$^1$H NMR (400 MHz, CDCl$_3$): δ 7.86 (d, J=8.3 Hz, 1H), 7.17 (d, J=7.8 Hz, 1H), 2.65 (s, 3H); MS (ES): m/z 278 (M+1).

f) 2-chloro-4-formyl-3-methylbenzonitrile

To a stirred solution of 2-chloro-4-iodo-3-methylbenzonitrile (30 g, 108.1 mmol) in dry THF at 0° C. was added isopropyl magnesium chloride (14.5 mL, 129.7 mmol, 2M solution in ether) drop wise under Nitrogen atmosphere and the reaction mixture was stirred for 2 h at 0° C. To this, 1-formyl piperidine (64.8 mL, 129.7 mmol) was added at 0° C. and stirred at same temperature for 2 h. The reaction mixture was quenched with sat. NH$_4$Cl solution and extracted with EtOAc. Organic layer was washed with water, brine, dried over Na$_2$SO$_4$ and concentrated. Crude product was purified by column chromatography using 8% ethylacetate in hexane as eluent.

Wt of the product: 14.5 g (75%)

$^1$H NMR (400 MHz, DMSO-$d_6$): δ10.32 (s, 1H), 8.03 (d, J=8.2 Hz, 1H), 7.92 (d, J=8.2 Hz, 1H), 2.71 (s, 3H); IR (KBr): 3072, 2962, 2927, 2856, 2237, 1707 cm$^{-1}$.

Building block B1

(2R,3S)-1-amino-3-(tert-butyldimethylsilyloxy)pyrrolidin-2-yl)methanol (BB-B1)

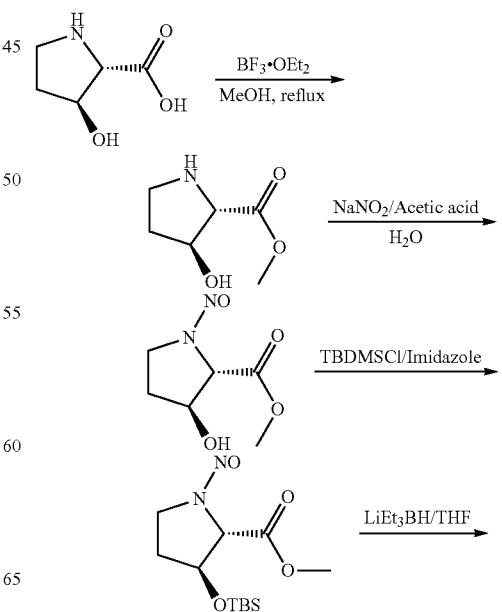

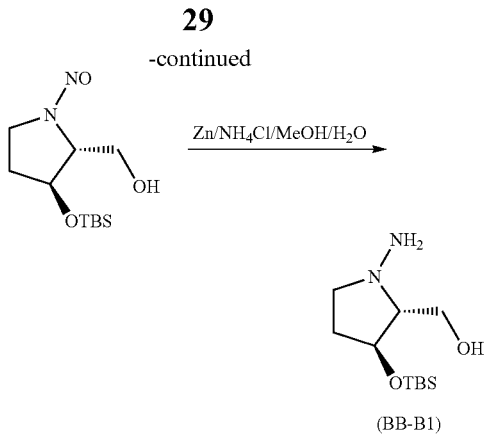

a) (2S,3S)-methyl 3-hydroxypyrrolidine-2-carboxylate

To a stirred solution of trans-3-hydroxy-L-proline (15 g, 0.114 moles) in methanol (200 mL) was added borontrifluoride diethyl ether (42 mL, 0.343 moles) and the reaction mixture was refluxed for 48 h. Once the starting material had disappeared (monitored by TLC) the reaction mixture was concentrated to get the title compound which was used in the next step without further purification.

Wt of the crude product: 16.6 g (99%)
MS (ES): m/z 146 (M+1)

b) (2S,3S)-methyl 3-hydroxy-1-nitrosopyrrolidine-2-carboxylate

To a solution of (2S,3S)-methyl 3-hydroxypyrrolidine-2-carboxylate (16 g, 0.110 moles) in water (60 mL) was added $NaNO_2$ (16 g, 0.220 moles) in water (30 mL) followed by the addition of glacial acetic acid (9.43 mL, 0.165 moles) at 0° C. and the reaction mixture was stirred for 4 h. Once the starting material had disappeared (monitored by TLC), the reaction mixture was diluted with ethyl acetate. The organic layer was washed with water, brine, dried over $Na_2SO_4$ and concentrated to get the title compound which was used in the next step without purification.

Wt of the crude product: 13 g (68%)
MS (ES): m/z 175 (M+1)

c) (2S,3S)-methyl 3-(tert-butyldimethylsilyloxy)-1-nitrosopyrrolidine-2-carboxylate To a solution of (2S,3S)-methyl 3-hydroxy-1-nitrosopyrrolidine-2-carboxylate (13 g, 0.0742 moles) in DCM (150 mL) at room temperature were added imidazole (15.2 g, 0.224 moles) and TBDMS-Cl (22.5 g, 0.149 moles) and the mixture was stirred at room temperature for 3 h. The reaction mixture was diluted with DCM and washed with water, brine, dried over $Na_2SO_4$ and concentrated. Purification by column chromatography over silica gel using 10% EtOAc in hexane as a solvent provided the title compound.

Wt of the product: 20 g (93%)
MS (ES): m/z 289.2 (M+1)

d) (2R,3S)-3-(tert-butyldimethylsilyloxy)-1-nitrosopyrrolidin-2-yl)methanol

To a solution of (2S,3S)-methyl 3-(tert-butyldimethylsilyloxy)-1-nitrosopyrrolidine-2-carboxylate (20 g, 0.0692 moles) in THF (350 mL) at −78° C. was added super hydride (207 mL, 0.207 moles, 1M Solution in THF) and stirred at room temperature for 5 h. The reaction mixture was poured over ice cold water and extracted with ethyl acetate. Organic layer was washed with water, brine, dried over $Na_2SO_4$ and concentrated. Purification by column chromatography over silica gel using 30% EtOAc in hexane as a solvent provided the title compound.

Wt of the product: 10.5 g (58%)
$^1$H NMR (400 MHz, DMSO-$d_6$): δ 5.08 (t, J=5.9 Hz, 1H), 4.43-4.42 (m, 1H), 4.21-4.09 (m, 1H), 3.66-3.59 (m, 2H), 3.57-3.40 (m, 2H), 2.16-2.07 (m, 1H), 1.75-1.72 (m, 1H), 0.76 (s, 9H), 0.03 (s, 3H), 0.02 (s, 3H); IR (KBr): 3309, 2953, 2929, 2858, 1469 cm$^{-1}$; MS (ES): m/z 261.1 (M+1).

e) (2R,3S)-1-amino-3-(tert-butyldimethylsilyloxy) pyrrolidin-2-yl)methanol

To a solution of (2R,3S)-3-(tert-butyldimethylsilyloxy)-1-nitrosopyrrolidin-2-yl)methanol (9.0 g, 0.034 moles) in methanol (140 mL) at room temperature were added Zn dust (23 g, 0.353 moles) and $NH_4Cl$ (28 g, 0.529 moles). After the addition was over, the reaction mixture was stirred at room temperature for 30 min and then at 50° C. for 1 h. Once the starting material had disappeared (monitored by TLC), the reaction mixture was cooled to room temperature, filtered and the filtrate was concentrated to give a liquid which was diluted with ethyl acetate. Organic layer was washed with water, brine, dried over $Na_2SO_4$ and concentrated to get the title compound.

Wt of the crude product: 7 g (83%)
MS (ES): m/z 247 (M+1)

Building block B2

((2S,4R)-1-amino-4-(tert-butyldimethylsilyloxy) pyrrolidin-2-yl)methanol (BB-B2)

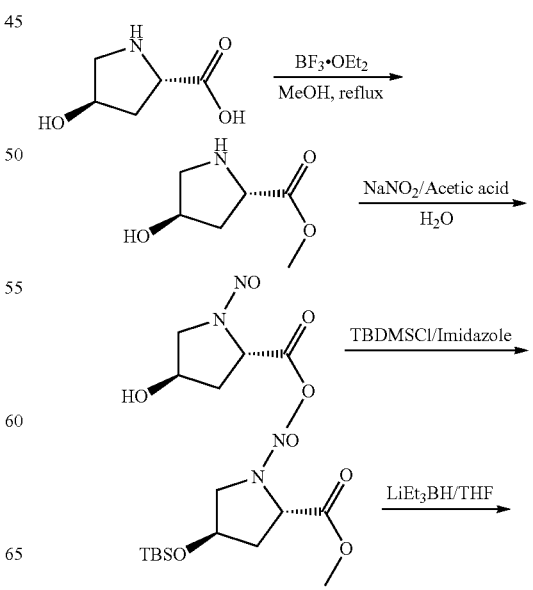

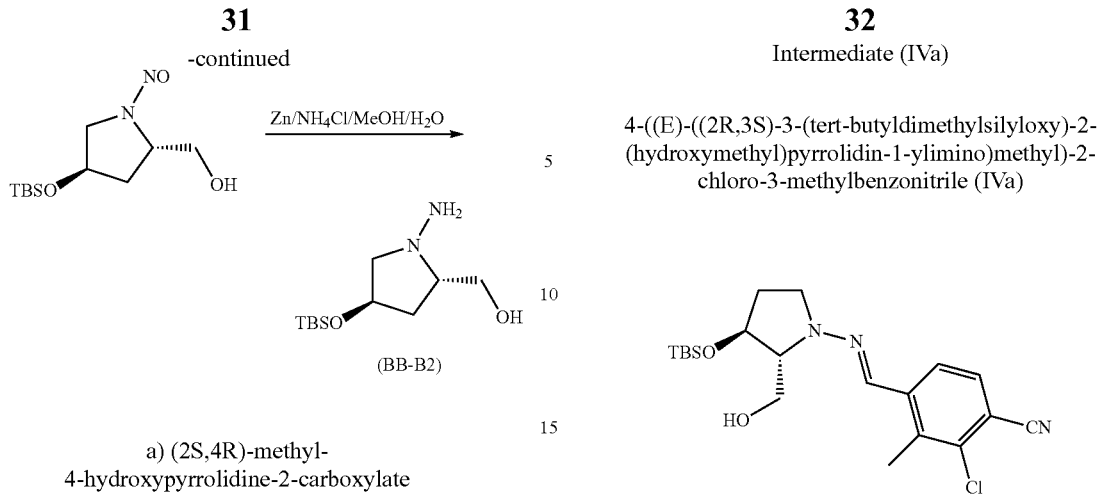

a) (2S,4R)-methyl-4-hydroxypyrrolidine-2-carboxylate

The title compound was synthesized using the same procedure as that for compound building block B1 step a).

MS (ES): m/z 146 (M+1)

b) (2S,4R)-methyl-4-hydroxy-1-nitrosopyrrolidine-2-carboxylate

The title compound was synthesized using the same procedure which was followed for building block B1 step b) by using (2S,4R)-methyl-4-hydroxypyrrolidine-2-carboxylate as starting material.

MS (ES): m/z 175 (M+1)

c) (2S,4R)-methyl-4-(tert-butyldimethylsilyloxy)-1-nitrosopyrrolidine-2-carboxylate The title compound was synthesized using the same procedure which was followed for building block B1 step c) using (2S,4R)-methyl-4-hydroxy-1-nitrosopyrrolidine-2-carboxylate as starting material.

$^1$H NMR (400 MHz, DMSO-$d_6$): δ 4.64-4.54 (m, 1H), 4.43 (t, J=8.83 Hz, 1H), 4.30-4.38 (m, 2H), 3.62 (s, 3H), 2.23-2.17 (m, 2H), 0.84 (s, 9H), 0.07 (s, 6H); MS (ES): m/z 289 (M+1).

d) ((2S,4R)-4-(tert-butyldimethylsilyloxy)-1-nitrosopyrrolidin-2-yl)methanol

The title compound was synthesized using the same procedure which was followed for building block B1 step d) using (2S,4R)-methyl-4-(tert-butyldimethylsilyloxy)-1-nitrosopyrrolidine-2-carboxylate as starting material.

$^1$H NMR (400 MHz, DMSO-$d_6$): δ 5.0 (m, 1H), 4.59-4.55 (m, 2H), 3.89-3.88 (m, 1H), 3.81-3.79 (m, 1H), 3.55-3.49 (m, 2H), 2.24-2.19 (m, 1H), 2.05-2.02 (m, 1H), 0.84 (s, 9H), 0.07 (s, 6H); MS (ES): m/z 261 (M+1).

e) ((2S,4R)-1-amino-4-(tert-butyldimethylsilyloxy)pyrrolidin-2-yl)methanol

The title compound was synthesized using the same procedure which was followed for building block B1 step e) using ((2S,4R)-4-(tert-butyldimethylsilyloxy)-1-nitrosopyrrolidin-2-yl)methanol as starting material.

MS (ES): m/z 247 (M+1)

Intermediate (IVa)

4-((E)-((2R,3S)-3-(tert-butyldimethylsilyloxy)-2-(hydroxymethyl)pyrrolidin-1-ylimino)methyl)-2-chloro-3-methylbenzonitrile (IVa)

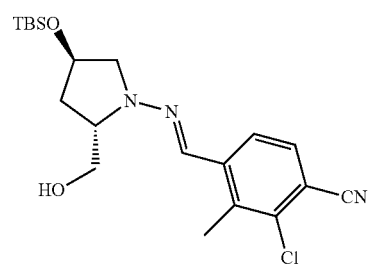 [SMILES: Cc1c(/C=N/N2C[C@H](O[Si](C)(C)C(C)(C)C)C[C@H]2CO)ccc(C#N)c1Cl]

A mixture of building block B1 (2R,3S)-1-amino-3-(tert-butyldimethylsilyloxy)pyrrolidin-2-yl)methanol (7 g, 0.028 moles) and building block A1 2-chloro-4-formyl-3-methylbenzonitrile (5.6 g, 0.0313 moles) in glacial acetic acid (60 mL) was stirred at room temperature for 3 h. Once both the starting materials disappeared (monitored by TLC), the reaction mixture was poured into ice water and extracted with EtOAc. The organic layer was washed with water, brine, dried over $Na_2SO_4$ and concentrated to give crude which was purified by column chromatography over silica gel using 15% EtOAc in hexane as a solvent to provide the title compound.

Wt of the product: 7.5 g (66%)

$^1$H NMR (400 MHz, DMSO-$d_6$): δ 7.77 (d, J=8.3 Hz, 1H), 7.65 (d, J=8.8 Hz, 1H), 7.20 (s, 1H), 4.87-4.85 (m, 1H), 4.38 (s, 1H), 3.61-3.59 (m, 1H), 3.58-3.41 (m, 3H), 3.29-3.24 (m, 1H), 2.44 (s, 3H), 2.23-2.08 (m, 1H), 1.89-1.85 (m, 1H), 0.85 (s, 9H), 0.09 (s, 3H), 0.08 (s, 3H); IR (KBr): 3473, 2945, 2854, 2233, 1522, 1523 cm$^{-1}$; MS (ES): m/z 408.3 (M+1).

Intermediate (IVb)

4-((E)-((2S,4R)-4-(tert-butyldimethylsilyloxy)-2-(hydroxymethyl)pyrrolidin-1-ylimino)methyl)-2-chloro-3-methylbenzonitrile (IVb)

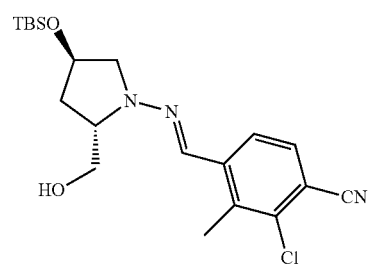 [SMILES: Cc1c(/C=N/N2C[C@H](O[Si](C)(C)C(C)(C)C)C[C@H]2CO)ccc(C#N)c1Cl]

The title compound was synthesized using the same procedure which was followed for intermediate IVa using building block B2 and building block A1 as starting materials.

$^1$H NMR (400 MHz, DMSO-$d_6$): δ 7.77 (d, J=8.3 Hz, 1H), 7.64 (d, J=9 Hz, 1H), 7.17 (s, 1H), 4.71-4.63 (m, 1H), 4.59 (bs, 1H), 3.82 (bs, 1H), 3.68-3.65 (m, 1H), 3.64-3.61 (m, 2H), 3.11 (d, J=3.4 Hz, 1H), 2.49 (s, 3H), 2.10-2.06 (m, 1H), 1.90-1.86 (m, 1H), 0.86 (s, 9H), 0.09 (s, 6H); MS (ES): m/z 408.2 (M+1).

Intermediate (IIIa)

4-((E)-((2S,3S)-3-(tert-butyldimethylsilyloxy)-2-formylpyrrolidin-1-ylimino)methyl)-2-chloro-3-methylbenzonitrile (IIIa)

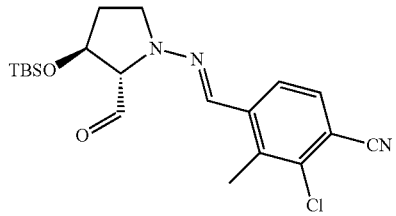 [SMILES: Cc1c(/C=N/N2CC[C@H](O[Si](C)(C)C(C)(C)C)[C@H]2C=O)ccc(C#N)c1Cl]

To a solution of oxalyl chloride (1.92 mL, 0.022 moles) in dry DCM (25 mL) at −78° C. was added DMSO (3.12 mL, 0.044 moles) and stirred for 30 min. Then to the reaction mixture at the same temperature was added a solution of 4-((E)-((2R,3S)-3-(tert-butyldimethylsilyloxy)-2-(hydroxymethyl)pyrrolidin-1-ylimino)methyl)-2-chloro-3-methylbenzonitrile (IVa) (7.5 g, 0.0184 moles) in 100 mL DCM and continued stirring for 1 h. The reaction mixture was quenched with triethylamine (13 mL) at −30° C. and stirred for 1 h. Then it was diluted with DCM and washed with water, brine, dried over Na$_2$SO$_4$ and concentrated to get the title compound which was used in the next step without further purification.

Wt of the crude product: 7.0 g (94%)

$^1$H NMR (400 MHz, DMSO-d$_6$): δ9.53 (d, J=1.9 Hz, 1H), 7.62 (d, J=8.3 Hz, 1H), 7.57 (d, J=8.3 Hz, 1H), 7.29 (s, 1H), 4.52-4.51 (m, 1H), 4.01 (s, 1H), 3.60-3.53 (m, 1H), 3.37-3.17 (m, 1H), 2.36 (s, 3H), 2.10-2.05 (m, 1H), 1.89-1.85 (m, 1H), 0.76 (s, 9H), 0.009 (s, 3H), 0.00 (s, 3H); IR (KBr): 2953, 2927, 2856, 2227, 1730, 1556 cm$^{-1}$; MS (ES): m/z 406.3 (M+1).

Intermediate (IIIb)

4-((E)-((2S,4R)-4-(tert-butyldimethylsilyloxy)-2-formylpyrrolidin-1-ylimino)methyl)-2-chloro-3-methylbenzonitrile (IIIb)

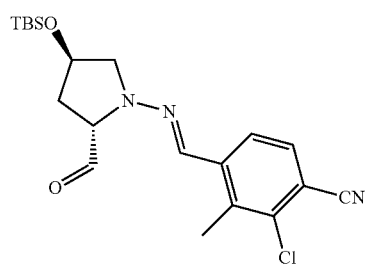 [SMILES: Cc1c(/C=N/N2C[C@H](O[Si](C)(C)C(C)(C)C)C[C@H]2C=O)ccc(C#N)c1Cl]

The title compound was synthesized using the same procedure which was followed for intermediate (IIIa) using intermediate (IVb) as starting material.

Intermediate (IIa)

4-((3S,3aR,4S)-4-(tert-butyldimethylsilyloxy)-3-hydroxy-3a,4,5,6-tetrahydro-3H-pyrrolo[1,2-b]pyrazol-2-yl)-2-chloro-3-methylbenzonitrile (IIa)

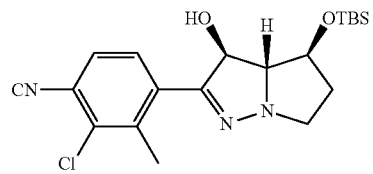

To a solution of intermediate (IIIa) 4-((E)-((2S,3S)-3-(tert-butyldimethylsilyloxy)-2-formylpyrrolidin-1-ylimino)methyl)-2-chloro-3-methylbenzonitrile (7.0 g, 0.0172 moles) in DCM (100 mL) at 0° C. was added borontrifluoride diethyl etherate (6.2 mL, 0.0207 moles) and reaction mixture was stirred at room temperature for 3 h. Once the starting material had disappeared (monitored by TLC), the reaction mixture was diluted with DCM, water and washed with saturated NaHCO$_3$ aqueous solution, water, brine, dried over Na$_2$SO$_4$ and concentrated to get the crude product. Purification of the crude by column chromatography over silica gel using 10% EtOAc in hexane as a solvent provided the title compound.

Wt of the product: 4.2 g (60%)

$^1$H NMR (400 MHz, DMSO-d$_6$): δ7.87 (d, J=8.3 Hz, 1H), 7.71 (d, J=8.3 Hz, 1H), 5.94 (d, J=6.8 Hz, 1H), 5.27 (d, J=7.3 Hz, 1H), 4.17-4.15 (m, 1H), 3.55-3.50 (m, 1H), 3.45-3.42 (m, 1H), 3.41-3.40 (m, 1H), 2.54 (s, 3H), 1.81-1.76 (m, 1H), 1.62-1.57 (m, 1H), 0.89 (s, 9H), 0.10 (s, 3H), 0.08 (s, 3H); MS (ES): m/z 406.3 (M+1).

Intermediate (IIb)

4-((3S,3aS,5R)-5-(tert-butyldimethylsilyloxy)-3-hydroxy-3a,4,5,6-tetrahydro-3H-pyrrolo[1,2-b]pyrazol-2-yl)-2-chloro-3-methylbenzonitrile (IIb)

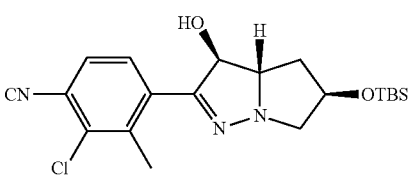

The title compound was synthesized using the same procedure which was followed for intermediate (IIa) using intermediate (IIIb) as starting material.

$^1$H NMR (400 MHz, DMSO-d$_6$): δ 7.85 (d, J=8.3 Hz, 1H), 7.70 (d, J=8.3 Hz, 1H), 5.78 (d, J=6.3 Hz, 1H), 5.10 (d, J=6.3 Hz, 1H), 4.39-4.37 (m, 1H), 3.84-3.80 (m, 1H), 3.69-3.65 (m,

1H), 3.20-3.16 (m, 1H), 2.54 (s, 3H), 1.73-1.72 (m, 1H), 1.64-1.61 (m, 1H), 0.86 (s, 9H), 0.05 (s, 6H); MS (ES): m/z 406.1 (M+1).

Example 1

2-chloro-4-((3S,3aS,4S)-4-hydroxy-3-methoxy-3a,4,5,6-tetrahydro-3H-pyrrolo[1,2-b]pyrazol-2-yl)-3-methylbenzonitrile

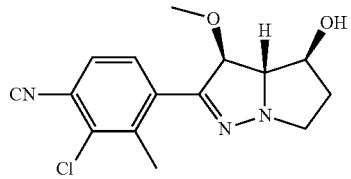

a) 4-((3S,3aR,4S)-4-(tert-butyldimethylsilyloxy)-3-methoxy-3a,4,5,6-tetrahydro-3H-pyrrolo[1,2-b]pyrazol-2-yl)-2-chloro-3-methylbenzonitrile To a solution of intermediate (IIa) 4-((3S,3aR,4S)-4-(tert-butyldimethylsilyloxy)-3-hydroxy-3a,4,5,6-tetrahydro-3H-pyrrolo[1,2-b]pyrazol-2-yl)-2-chloro-3-methylbenzonitrile (500 mg, 1.234 mmol) in THF (10 mL) at 0° C. was added NaH (99 mg, 1.851 mmol) and the reaction mixture was stirred for 30 min. Methyliodide (0.11 mL, 2.469 mmol) was added to the reaction mixture at 0° C. and it was stirred at room temperature for 3 h. Reaction mixture was poured over ice cold water and extracted with ethyl acetate. Organic layer was washed with water, brine, dried over $Na_2SO_4$ and concentrated. Purification by column chromatography over silica gel using 10% EtOAc in hexane provided the title compound.

Wt of the product: 0.42 g (82%)

$^1$H NMR (400 MHz, DMSO-$d_6$): δ 7.88 (d, J=7.8 Hz, 1H), 7.68 (d, J=8.3 Hz, 1H), 5.20 (s, 1H), 4.16 (q, J=4.9 Hz, 1H), 3.55-3.45 (m, 3H), 3.22 (s, 3H), 2.55 (s, 3H), 1.88-1.81 (m, 1H), 1.69-1.62 (m, 1H), 0.89 (s, 9H), 0.11 (s, 3H), 0.09 (s, 3H); MS (ES): m/z 420.3 (M+1).

b) 2-chloro-4-((3S,3aS,4S)-4-hydroxy-3-methoxy-3a,4,5,6-tetrahydro-3H-pyrrolo[1,2-b]pyrazol-2-yl)-3-methylbenzonitrile To a solution of 4-((3S,3aR,4S)-4-(tert-butyldimethylsilyloxy)-3-methoxy-3a,4,5,6-tetrahydro-3H-pyrrolo[1,2-b]pyrazol-2-yl)-2-chloro-3-methylbenzonitrile (400 mg, 0.954 mmol) in THF (10 mL) at 0° C. was added tetra butyl ammonium fluoride (1.9 mL, 1.909 mmol, 1M solution in THF) and the reaction mixture was stirred at room temperature for 3 h. Once the starting material had disappeared (monitored by TLC), reaction mixture was diluted with ethyl acetate and the organic layer was washed with water, brine, dried over $Na_2SO_4$ and concentrated to get the crude product. The product was purified by column chromatography over silica gel using 2% MeOH in DCM as solvent to provide the title compound. The absolute stereochemistry was confirmed by X-ray crystallography.

Wt of the product: 190 mg (62%)

$^1$H NMR (400 MHz, $CDCl_3$+DMSO-$d_6$): δ 7.53-7.37 (m, 2H), 5.09 (s, 1H), 4.68 (d, J=4.5 Hz, 1H), 3.99-3.95 (m, 1H), 3.66-3.65 (m, 3H), 3.31 (s, 3H), 2.61 (s, 3H), 2.58 (s, 1H), 2.05-1.95 (m, 1H), 1.90-1.82 (m, 1H); IR (KBr): 3387, 3311, 3234, 2933, 2821, 2231, 1589 cm$^{-1}$; MS (ES): m/z 306.2 (M+1).

Example 2

2-chloro-4-((3S,3aS,4R)-4-hydroxy-3-methoxy-3a,4,5,6-tetrahydro-3H-pyrrolo[1,2-b]pyrazol-2-yl)-3-methylbenzonitrile

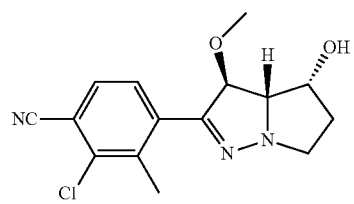 [SMILES: CO[C@@H]1C(c2ccc(C#N)c(Cl)c2C)=NN2CC[C@@H](O)[C@@H]12]

a) (3S,3aS,4R)-2-(3-chloro-4-cyano-2-methylphenyl)-3-methoxy-3a,4,5,6-tetrahydro-3H-pyrrolo[1,2-b]pyrazol-4-yl benzoate To a solution of 2-chloro-4-((3S,3aS,4S)-4-hydroxy-3-methoxy-3a,4,5,6-tetrahydro-3H-pyrrolo[1,2-b]pyrazol-2-yl)-3-methylbenzonitrile obtained by the procedure of example 1 (60 mg, 0.196 mmol) in THF (2 mL) were added $PPh_3$ (77 mg, 0.295 mmol), benzoic acid (36 mg, 0.295 mmol) and DIAD (0.05 mL, 0.295 mmol) and the reaction mixture was stirred at room temperature for 3 h. Once the starting material had disappeared (monitored by TLC), the reaction mixture was diluted with ethyl acetate. The organic layer was washed with saturated $NaHCO_3$ solution, water, brine and dried over $Na_2SO_4$ and concentrated to get the title compound which was used in the next step without further purification.

Wt of the crude product: 80 mg (yield) 100%

MS (ES): m/z 410 (M+1).

b) 2-chloro-4-((3S,3aS,4R)-4-hydroxy-3-methoxy-3a,4,5,6-tetrahydro-3H-pyrrolo[1,2-b]pyrazol-2-yl)-3-methylbenzonitrile To a solution of (3S,3aS,4R)-2-(3-chloro-4-cyano-2-methylphenyl)-3-methoxy-3a,4,5,6-tetrahydro-3H-pyrrolo[1,2-b]pyrazol-4-yl benzoate (80 mg, 0.0.195 mmol) in THF (2 mL) at 0° C. was added a solution of LiOH.$H_2O$ (25 mg, 0.586 mmol) in water and the reaction mixture was stirred at room temperature for overnight. Once the starting material had disappeared (monitored by TLC), reaction mixture was extracted with ethyl acetate. Organic layer was washed with saturated $NaHCO_3$ solution, water, and brine and then dried over $Na_2SO_4$ and concentrated. Purification of the crude by column chromatography over silica gel using 2% MeOH in DCM provided the title compound.

Wt of the product: 30 mg (50%)

$^1$H NMR (400 MHz, $CDCl_3$+DMSO-$d_6$): δ 7.52 (bs, 2H), 5.39 (d, J=1.4 Hz, 1H), 4.54-4.50 (m, 1H), 3.79-3.70 (m, 1H), 3.68-3.64 (m, 1H), 3.57-3.51 (m, 1H), 3.26 (s, 3H), 2.61 (s,

3H), 2.19-2.1 (m, 1H), 1.91-1.87 (m, 1H), 1.86 (d, J=4.9 Hz, 1H); IR (KBr): 3450, 2935, 2231, 1589 cm$^{-1}$; MS (ES): m/z 306.1 (M+1).

Example 3

2-chloro-4-((3S,3aS,4S)-3,4-dihydroxy-3a,4,5,6-tetrahydro-3H-pyrrolo[1,2-b]pyrazol-2-yl)-3-methyl-benzonitrile

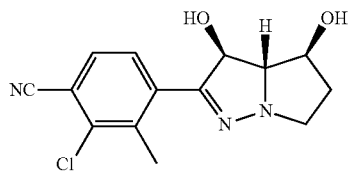

To a solution of intermediate (IIa) 4-((3S,3aR,4S)-4-(tert-butyldimethylsilyloxy)-3-hydroxy-3a,4,5,6-tetrahydro-3H-pyrrolo[1,2-b]pyrazol-2-yl)-2-chloro-3-methylbenzonitrile (50 mg, 0.1233 mmol) in THF (2 mL) at 0° C. was added tetrabutylammonium fluoride (0.24 mL, 0.246 mmol, 1M solution in THF) and reaction mixture was stirred at room temperature for 3 h. Once the starting material had disappeared (monitored by TLC), it was diluted with ethyl acetate and washed with water, brine, dried over Na$_2$SO$_4$ and concentrated. Purification by column chromatography over silica gel using 3% MeOH in DCM as solvent provided the title compound.
Wt of the product: 10 mg (28%)
$^1$H NMR (400 MHz, DMSO-d$_6$): δ 7.85 (d, J=8.2 Hz, 1H), 7.69 (d, J=8.2 Hz, 1H), 5.87 (d, J=6.7 Hz, 1H), 5.26 (d, J=6.4 Hz, 1H), 5.15 (d, J=4.2 Hz, 1H), 3.93-3.80 (m, 1H), 3.48-3.43 (m, 2H), 3.40-3.34 (m, 1H), 2.53 (s, 3H), 1.81-1.74 (m, 1H), 1.62-1.61 (m, 1H); IR (KBr): 3442, 3363, 2951, 2239, 1587, 1568 cm$^{-1}$; MS (ES): m/z 292.1 (M+1)

Example 4

2-chloro-4-((3S,3aS,4R)-3,4-dihydroxy-3a,4,5,6-tetrahydro-3H-pyrrolo[1,2-b]pyrazol-2-yl)-3-methyl-benzonitrile

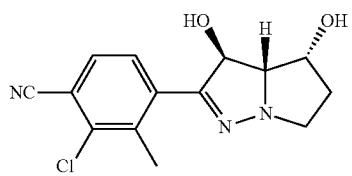

a) 4-((3S,3aR,4S)-4-(tert-butyldimethylsilyloxy)-3-(tetrahydro-2H-pyran-2-yloxy)-3a,4,5,6-tetrahydro-3H-pyrrolo[1,2-b]pyrazol-2-yl)-2-chloro-3-methyl-benzonitrile To a solution of intermediate (IIa) 4-((3S,3aR,4S)-4-(tert-butyldimethylsilyloxy)-3-hydroxy-3a,4,5,6-tetrahydro-3H-pyrrolo[1,2-b]pyrazol-2-yl)-2-chloro-3-methylbenzonitrile (150 mg, 0.370 mmol) in DCM was added 3,4-dihydro-2H-pyran (34 mg, 0.407 mmol) followed by the addition of PPTS (93 mg, 0.370 mmol) and the reaction mixture was stirred at room temperature for 16 h. Reaction mixture was extracted with DCM and the DCM layer was washed with water, brine, dried over Na$_2$SO$_4$ and concentrated. Purification of the crude by column chromatography over silica gel using 10% EtOAc in hexane provided the title compound.
Wt of the product: 120 mg (66%)
MS (ES): m/z 490.2 (M+1)

b) 2-chloro-4-((3S,3aS,4S)-4-hydroxy-3-(tetrahydro-2H-pyran-2-yloxy)-3a,4,5,6-tetrahydro-3H-pyrrolo[1,2-b]pyrazol-2-yl)-3-methylbenzonitrile To a solution of 4-((3S,3aR,4S)-4-(tert-butyldimethylsilyloxy)-3-(tetrahydro-2H-pyran-2-yloxy)-3a,4,5,6-tetrahydro-3H-pyrrolo[1,2-b]pyrazol-2-yl)-2-chloro-3-methylbenzonitrile (120 mg, 0.245 mmol) in THF (2 mL) at 0° C. was added tetrabutylammonium fluoride (0.49 mL, 0.490 mmol, 1M solution in THF) and the reaction mixture was stirred at room temperature for 3 h. Once the starting material had disappeared (monitored by TLC), it was diluted with ethyl acetate and the organic layer was washed with water, brine, dried over Na$_2$SO$_4$ and concentrated. Purification of crude by column chromatography over silica gel using 30% EtOAc in hexane provided the title compound.
Wt of the product: 80 mg (96%)
MS (ES): m/z 376.2 (M+1)

c) (3S,3aS,4R)-2-(3-chloro-4-cyano-2-methylphenyl)-3-(tetrahydro-2H-pyran-2-yloxy)-3a,4,5,6-tetrahydro-3H-pyrrolo[1,2-b]pyrazol-4-yl benzoate To a solution of 2-chloro-4-((3S,3aS,4S)-4-hydroxy-3-(tetrahydro-2H-pyran-2-yloxy)-3a,4,5,6-tetrahydro-3H-pyrrolo[1,2-b]pyrazol-2-yl)-3-methylbenzonitrile (80 mg, 0.235 mmol) in THF (3 mL) were added PPh$_3$ (123 mg, 0.470 mmol), benzoic acid (58 mg, 0.470 mmol) and DIAD (0.09 mL, 0.470 mmol) and the reaction mixture was stirred at room temperature for 3 h. Then it was diluted with ethyl acetate and washed with saturated NaHCO$_3$ solution, water, and brine, then dried over Na$_2$SO$_4$ and concentrated to get the crude product which was used in the next step without purification.
Wt of the crude product: 102 mg (yield 100%)
MS (ES): m/z 480.2 (M+1).

d) 2-chloro-4-((3S,3aS,4R)-4-hydroxy-3-(tetrahydro-2H-pyran-2-yloxy)-3a,4,5,6-tetrahydro-3H-pyrrolo[1,2-b]pyrazol-2-yl)-3-methylbenzonitrile To a solution of (3S,3aS,4R)-2-(3-chloro-4-cyano-2-methylphenyl)-3-(tetrahydro-2H-pyran-2-yloxy)-3a,4,5,6-tetrahydro-3H-pyrrolo[1,2-b]pyrazol-4-yl benzoate (100 mg, 0.208 mmol) in THF (2 mL) at 0° C. was added a solution of LiOH.H$_2$O (25 mg, 0.586 mmol) in water (1 mL) and the reaction mixture was stirred at room temperature for overnight. Once the starting material had disappeared (monitored by TLC), reaction mixture was extracted with ethyl acetate. Organic layer was washed with water and brine then dried over Na$_2$SO$_4$ and concentrated to get the crude product which was used in the next step without further purification.
Wt of the crude product: 70 mg (yield: 90%)
MS (ES): m/z 376.1 (M+1).

e) 2-chloro-4-((3S,3aS,4R)-3,4-dihydroxy-3a,4,5,6-tetrahydro-3H-pyrrolo[1,2-b]pyrazol-2-yl)-3-methyl-benzonitrile To a stirred solution of 2-chloro-4-((3S,3aS,4R)-4-hydroxy-3-(tetrahydro-2H-pyran-2-yloxy)-3a,4,5,6-tetrahydro-3H-pyrrolo[1,2-b]pyrazol-2-yl)-3-methylbenzonitrile (30 mg, 0.088 mmol) in methanol (1 mL) was added p-toluenesulfonic acid (20 mg, 0.1058 mmol) and the reaction mixture was stirred at room temperature for overnight. Methanol was evaporated from reaction mixture and extracted with EtOAc. Organic layer was washed with water, brine, dried over Na$_2$SO$_4$ and concentrated. Purification by column chromatography over silica gel using 3% MeOH in DCM provided the title compound.

Wt of the product: 6 mg (23%)

$^1$H NMR (400 MHz, DMSO-d$_6$): δ 7.84 (d, J=7.9 Hz, 1H), 7.61 (d, J=7.9 Hz, 1H), 5.68 (d, J=7.3 Hz, 1H), 5.39 (d, J=6.1 Hz, 1H), 5.01 (d, J=3.9 Hz, 1H), 4.28 (t, J=3.9 Hz, 1H), 3.51 (d, J=4.2 Hz, 1H), 3.45-3.34 (m, 2H), 2.54 (s, 3H), 1.95-1.91 (m, 1H), 1.69-1.68 (m, 1H); MS (ES): m/z 292.1 (M+1)

Example 5

2-chloro-4-((3S,3aS,4S)-3-ethoxy-4-hydroxy-3a,4,5,6-tetrahydro-3H-pyrrolo[1,2-b]pyrazol-2-yl)-3-methylbenzonitrile

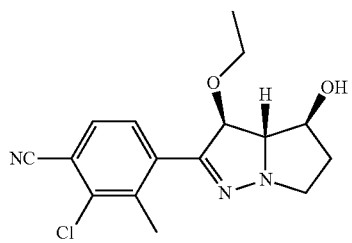 [SMILES: CCO[C@@H]1C(c2ccc(C#N)c(Cl)c2C)=NN2CC[C@H](O)[C@@H]12]

a) 4-((3S,3aR,4S)-4-(tert-butyldimethylsilyloxy)-3-ethoxy-3a,4,5,6-tetrahydro-3H-pyrrolo[1,2-b]pyrazol-2-yl)-2-chloro-3-methylbenzonitrile The title compound was synthesized in a method analogous to that described in example 1a) by replacing methyl iodide with ethyl iodide.

Wt of the product: 72 mg (67%)

$^1$H NMR (400 MHz, CDCl$_3$): δ 7.54-7.48 (m, 2H), 5.00 (d, J=1.5 Hz, 1H), 3.91-3.89 (m, 1H), 3.69-3.63 (m, 3H), 3.53-3.43 (m, 2H), 2.61 (s, 3H), 2.02-1.90 (m, 1H), 1.82-1.79 (m, 1H), 1.18 (t, J=6.8 Hz, 3H), 0.91 (s, 9H), 0.09 (s, 3H), 0.08 (s, 3H); MS (ES): m/z 434.1 (M+1).

b) 2-chloro-4-((3S,3aS,4S)-3-ethoxy-4-hydroxy-3a,4,5,6-tetrahydro-3H-pyrrolo[1,2-b]pyrazol-2-yl)-3-methylbenzonitrile The title compound was synthesized in a method analogous to that described in example 1b) using 4-((3S,3aR,4S)-4-(tert-butyldimethylsilyloxy)-3-ethoxy-3a,4,5,6-tetrahydro-3H-pyrrolo[1,2-b]pyrazol-2-yl)-2-chloro-3-methylbenzonitrile as starting material.

Wt of the product: 30 mg (56%)

$^1$H NMR (400 MHz, DMSO-d$_6$): δ 7.86 (d, J=8.3 Hz, 1H), 7.65 (d, J=8.3 Hz, 1H), 5.26-5.21 (m, 2H), 3.94 (bs, 1H), 3.50-3.40 (m, 5H), 2.54 (s, 3H), 1.83-1.78 (m, 1H), 1.67-1.65 (m, 1H), 1.07 (t, J=6.9 Hz, 3H); IR (KBr): 3180, 2951, 2233, 1589, 1384, 1089 cm$^{-1}$; MS (ES): m/z 320 (M+1).

Example 6

2-chloro-4-((3S,3aS,4R)-3-ethoxy-4-hydroxy-3a,4,5,6-tetrahydro-3H-pyrrolo[1,2-b]pyrazol-2-yl)-3-methylbenzonitrile

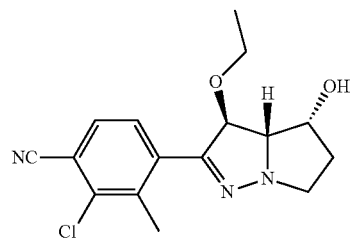 [SMILES: CCO[C@@H]1C(c2ccc(C#N)c(Cl)c2C)=NN2CC[C@@H](O)[C@@H]12]

a) (3S,3aS,4R)-2-(3-chloro-4-cyano-2-methylphenyl)-3-ethoxy-3a,4,5,6-tetrahydro-3H-pyrrolo[1,2-b]pyrazol-4-yl benzoate The title compound was synthesized in a method analogous to that described for example 2a) by using 2-chloro-4-((3S,3aS,4S)-3-ethoxy-4-hydroxy-3a,4,5,6-tetrahydro-3H-pyrrolo[1,2-b]pyrazol-2-yl)-3-methylbenzonitrile obtained by the procedure of example 5 as starting material.

Wt of the crude product: 60 mg (yield 100%)
MS (ES): m/z 424 (M+1).

b) 2-chloro-4-((3S,3aS,4R)-3-ethoxy-4-hydroxy-3a,4,5,6-tetrahydro-3H-pyrrolo[1,2-b]pyrazol-2-yl)-3-methylbenzonitrile The title compound was synthesized in a method analogous to that described for example 2b) using (3S,3aS,4R)-2-(3-chloro-4-cyano-2-methylphenyl)-3-ethoxy-3a,4,5,6-tetrahydro-3H-pyrrolo[1,2-b]pyrazol-4-yl benzoate as starting material.

Wt of the product: 8 mg (35%)

$^1$H NMR (400 MHz, CDCl$_3$+DMSO-d$_6$): δ 7.56-7.51 (m, 2H), 5.44 (s, 1H), 4.44 (bs, 1H), 4.13 (s, 1H), 3.75-3.73 (m, 1H), 3.66-3.62 (m, 1H), 3.51-3.42 (m, 3H), 2.62 (s, 3H), 2.17-2.04 (m, 1H), 1.89-1.85 (m, 1H), 1.16-1.12 (m, 3H); IR (KBr): 3444, 2972, 2929, 2231, 1589, 1589 cm$^{-1}$; MS (ES): m/z 320.2 (M+1).

Example 7

2-chloro-4-((3S,3aS,4S)-4-hydroxy-3-isopropoxy-3a,4,5,6-tetrahydro-3H-pyrrolo[1,2-b]pyrazol-2-yl)-3-methylbenzonitrile

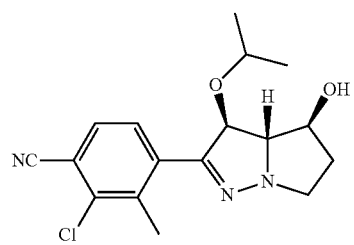

a) 4-((3S,3aR,4S)-4-(tert-butyldimethylsilyloxy)-3-isopropoxy-3a,4,5,6-tetrahydro-3H-pyrrolo[1,2-b]pyrazol-2-yl)-2-chloro-3-methylbenzonitrile The title compound is synthesized in a method analogous to that described for example 1a) by replacing methyl iodide with isopropyl iodide.

Wt of the product: 18 mg (16%)

$^1$H NMR (400 MHz, CDCl$_3$): δ 7.52 (d, J=7.9 Hz, 1H), 7.43 (d, J=8.3 Hz, 1H), 4.99 (s, 1H), 3.89-3.86 (m, 1H), 3.71-3.67 (m, 2H), 3.65-3.58 (m, 2H), 2.59 (s, 3H), 2.04-2.00 (m, 1H), 1.84-1.79 (m, 1H), 1.18 (d, J=5.9 Hz, 3H), 1.13 (d, J=5.9 Hz, 3H), 0.91 (s, 9H), 0.09 (s, 3H), 0.08 (s, 3H); MS (ES): m/z 448.4 (M+1).

b) 2-chloro-4-((3S,3aS,4S)-4-hydroxy-3-isopropoxy-3a,4,5,6-tetrahydro-3H-pyrrolo[1,2-b]pyrazol-2-yl)-3-methylbenzonitrile The title compound was synthesized in a method analogous to that described for example 1b) using 4-((3S,3aR,4S)-4-(tert-butyldimethylsilyloxy)-3-isopropoxy-3a,4,5,6-tetrahydro-3H-pyrrolo[1,2-b]pyrazol-2-yl)-2-chloro-3-methylbenzonitrile as starting material.

Wt of the product: 5 mg (43%)

$^1$H NMR (400 MHz, CDCl$_3$): δ7.53 (d, J=8.4 Hz, 1H), 7.45 (d, J=7.8 Hz, 1H), 5.08 (s, 1H), 4.09 (bs, 1H), 3.75-3.66 (m, 4H), 2.58 (s, 3H), 2.07-2.01 (m, 1H), 1.85-1.80 (m, 1H), 1.78 (bs, 1H), 1.18 (d, J=6.3 Hz, 3H), 1.14 (d, J=5.9 Hz, 3H); MS (ES): m/z 334.2 (M+1).

Example 8

2-chloro-4-((3S,3aS,5R)-5-hydroxy-3-methoxy-3a,4,5,6-tetrahydro-3H-pyrrolo[1,2-b]pyrazol-2-yl)-3-methylbenzonitrile

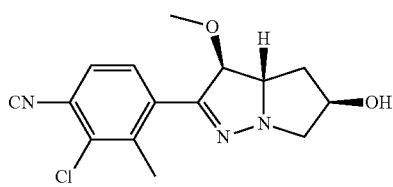

a) 4-((3S,3aS,5R)-5-(tert-butyldimethylsilyloxy)-3-methoxy-3a,4,5,6-tetrahydro-3H-pyrrolo[1,2-b]pyrazol-2-yl)-2-chloro-3-methylbenzonitrile The title compound was synthesized using the same procedure which was followed for example 1a) using intermediate (IIb) as starting material.

MS (ES): m/z 420 (M+1)

b) 2-chloro-4-((3S,3aS,5R)-5-hydroxy-3-methoxy-3a,4,5,6-tetrahydro-3H-pyrrolo[1,2-b]pyrazol-2-yl)-3-methylbenzonitrile The title compound was synthesized using the same procedure which was followed for example 1b) using 4-((3S,3aS,5R)-5-(tert-butyldimethylsilyloxy)-3-methoxy-3a,4,5,6-tetrahydro-3H-pyrrolo[1,2-b]pyrazol-2-yl)-2-chloro-3-methylbenzonitrile as starting material.

$^1$H NMR (400 MHz, DMSO-d$_6$): δ 7.86 (d, J=8.3 Hz, 1H), 7.65 (d, J=8.3 Hz, 1H), 5.05 (d, J=14.2 Hz, 1H), 5.03 (d, J=3.6 Hz, 1H), 4.30-4.20 (m, 1H), 4.03-3.99 (m, 1H), 3.67-3.63 (m, 1H), 3.29-3.22 (m, 1H), 3.19 (s, 3H), 2.54 (s, 3H), 1.81-1.77 (m, 1H), 1.59-1.55 (m, 1H); IR (KBr): 3408, 2947, 2831, 2229, 1587, 1527 cm$^{-1}$; MS (ES): m/z 306.5 (M+1)

Example 9

2-chloro-4-((3S,3aS)-3-methoxy-5-oxo-3a,4,5,6-tetrahydro-3H-pyrrolo[1,2-b]pyrazol-2-yl)-3-methylbenzonitrile

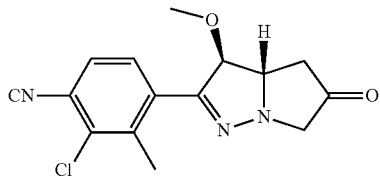

To a solution of 2-chloro-4-((3S,3aS,5R)-5-hydroxy-3-methoxy-3a,4,5,6-tetrahydro-3H-pyrrolo[1,2-b]pyrazol-2-yl)-3-methylbenzonitrile obtained by the procedure of example 8 (18 mg, 0.059 mmol) in DCM (2 mL) at rt was added Dess-Martin periodinane (50 mg, 0.118 mmol) and the reaction mixture was stirred at room temperature for 24 h. Once the starting material had disappeared (monitored by TLC), reaction mixture was diluted with DCM and washed with water, brine, dried over Na$_2$SO$_4$ and concentrated. Purification by preparative TLC method (2% MeOH in DCM) provided the title compound.

Wt of the product: 13 mg (86%)

$^1$H NMR (400 MHz, DMSO-d$_6$): δ 7.90 (d, J=7.9 Hz, 1H), 7.75 (d, J=8.3 Hz, 1H), 5.16 (s, 1H), 4.43 (t, J=9.7 Hz, 1H), 3.92 (d, J=19.1 Hz, 1H), 3.81 (d, J=18.6 Hz, 1H), 3.29 (s, 3H), 2.57 (s, 3H), 2.37-2.32 (m, 2H); IR (KBr): 2947, 2831, 2229, 1587 cm$^{-1}$; MS (ES): m/z 304 (M+1).

Example 10

2-chloro-4-((3S,3aS,5R)-3,5-dihydroxy-3a,4,5,6-tetrahydro-3H-pyrrolo[1,2-b]pyrazol-2-yl)-3-methylbenzonitrile

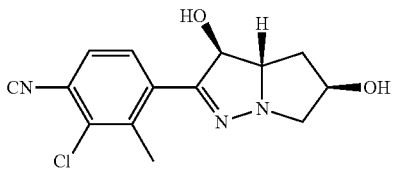

The title compound was synthesized using the same procedure which was followed for example 3 using intermediate (IIb) as starting material.

$^1$H NMR (400 MHz, DMSO-d$_6$): δ 7.85 (d, J=7.9 Hz, 1H), 7.70 (d, J=7.9 Hz, 1H), 5.75 (d, J=6.7 Hz, 1H), 5.08 (d, J=6.7 Hz, 1H), 4.95 (d, J=3.9 Hz, 1H), 4.23-4.22 (m, 1H), 3.83-3.80 (m, 1H), 3.65-3.62 (m, 1H), 3.21-3.18 (m, 3 Hz), 2.54 (s, 1H), 2.63 (s, 3H), 1.76-1.72 (m, 1H), 1.54-1.48 (m, 1H), IR (KBr): 3288, 3169, 2949, 2235, 1587 cm$^{-1}$; MS (ES): m/z 292.3 (M+1).

Example 11

2-chloro-4-((3S,3aS)-5-hydroxy-3-methoxy-5-(trifluoromethyl)-3a,4,5,6-tetrahydro-3H-pyrrolo[1,2-b]pyrazol-2-yl)-3-methylbenzonitrile

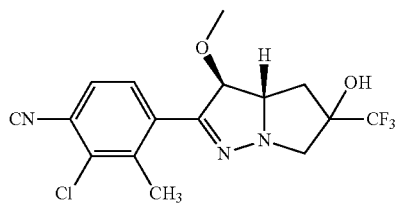

To a solution of 2-chloro-4-((3S,3aS)-3-methoxy-5-oxo-3a,4,5,6-tetrahydro-3H-pyrrolo[1,2-b]pyrazol-2-yl)-3-methylbenzonitrile prepared according to example 9 (10 mg, 0.033 mmole) in THF (3 mL) at 0° C. was added trifluoromethyl-trimethyl silane (0.02 mL, 0.0396 mmol) followed by the addition of CsF (0.5 mg, 0.0033 mmol) and the reaction mixture was stirred at room temperature for 3 h. Once the starting material had disappeared (monitored by TLC), the reaction mixture was quenched with 4N HCl and extracted with diethyl ether. Organic layer was washed with water, brine, dried over Na$_2$SO$_4$ and concentrated. Purification by preparative TLC method (2% MeOH in DCM) provided the title compound.

Wt of the product: 4 mg (33%)

$^1$H NMR (400 MHz, DMSO-d$_6$): δ 7.89 (d, J=8.3 Hz, 1H), 7.65 (d, J=8.3 Hz, 1H), 6.20 (bs, 1H), 5.16 (s, 1H), 4.10 (t, J=6.9 Hz, 1H), 3.78 (d, J=13.1 Hz, 1H), 3.49 (d, J=7.3 Hz, 1H), 3.43 (d, J=12.8 Hz, 1H), 3.24 (s, 3H), 2.59 (s, 3H), 1.92 (d, J=5.9 Hz, 1H); IR (KBr): 3338, 2918, 2848, 2233, 1587 cm$^{-1}$; MS (ES): m/z 374.2 (M+1).

Example 12

2-chloro-4-((3S,3aR,4R)-4-fluoro-3-methoxy-3a,4,5,6-tetrahydro-3H-pyrrolo[1,2-b]pyrazol-2-yl)-3-methylbenzonitrile

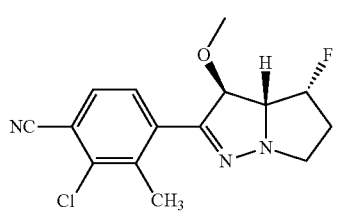 [SMILES: CO[C@@H]1C(c2ccc(C#N)c(Cl)c2C)=NN2CC[C@@H](F)[C@@H]12]

To a solution of 2-chloro-4-((3S,3aS,4S)-4-hydroxy-3-methoxy-3a,4,5,6-tetrahydro-3H-pyrrolo[1,2-b]pyrazol-2-yl)-3-methylbenzonitrile prepared according to example 1 (30 mg, 0.0983 mmol) in DCM (2 mL) at 0° C. was added DAST (0.02 mL, 0.1475 mmol) and the reaction mixture was stirred at same temperature for 2 h. Once the starting material had disappeared (monitored by TLC), reaction mixture was diluted with DCM, water and extracted. Organic layer was washed with water, brine, dried over Na$_2$SO$_4$ and concentrated. Purification by preparative TLC method (40% EtOAc in hexane) provided the title compound.

Wt of the product: 12 mg (40%)

$^1$H NMR (400 MHz, CDCl$_3$): δ7.54-7.49 (m, 2H), 5.30 (s, 1H), 5.25 (d, J=52.8 Hz, 1H), 3.84 (d, J=29.4 Hz, 1H), 3.80-3.66 (m, 2H), 3.28 (s, 3H), 2.59 (s, 3H), 2.35-2.10 (m, 2H); MS (ES): m/z 308 (M+1).

Example 13

2-chloro-4-((3S,3aR,4S)-4-fluoro-3-methoxy-3a,4,5,6-tetrahydro-3H-pyrrolo[1,2-b]pyrazol-2-yl)-3-methylbenzonitrile

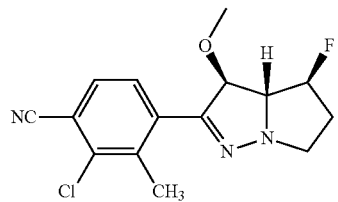 [SMILES: CO[C@@H]1C(c2ccc(C#N)c(Cl)c2C)=NN2CC[C@H](F)[C@@H]12]

The title compound was synthesized in a method similar to that described in example 12, by using 2-chloro-4-((3S,3aS,4R)-4-hydroxy-3-methoxy-3a,4,5,6-tetrahydro-3H-pyrrolo[1,2-b]pyrazol-2-yl)-3-methylbenzonitrile prepared according to example 2 as starting material.

$^1$H NMR (400 MHz, CDCl$_3$): δ 7.55-7.48 (m, 2H), 5.12 (s, 1H), 5.02 (dd, J=5.3 Hz, 53.7 Hz, 1H), 3.99 (d, J=27.4 Hz, 1H), 3.90-3.85 (m, 1H), 3.61-3.53 (m, 1H), 3.33 (s, 3H), 2.60 (s, 3H), 2.12-2.02 (m, 1H), 1.84-1.67 (m, 1H); MS (ES): m/z 308 (M+1).

Example 14

2-chloro-4-((3S,3aS,5S)-5-fluoro-3-methoxy-3a,4,5,6-tetrahydro-3H-pyrrolo[1,2-b]pyrazol-2-yl)-3-methylbenzonitrile

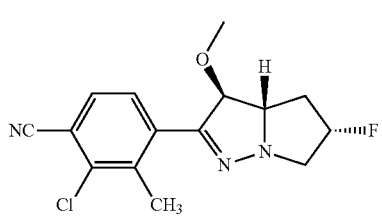 [SMILES: CO[C@@H]1C(c2ccc(C#N)c(Cl)c2C)=NN2C[C@@H](F)C[C@@H]12]

The title compound was synthesized in a method similar to that described in example 12, by using 2-chloro-4-((3S,3aS,5R)-5-hydroxy-3-methoxy-3a,4,5,6-tetrahydro-3H-pyrrolo[1,2-b]pyrazol-2-yl)-3-methylbenzonitrile prepared according to example 8 as starting material.

$^1$H NMR (400 MHz, DMSO-d$_6$): δ 7.87 (d, J=8.3 Hz, 1H), 7.66 (d, J=8.3 Hz, 1H), 5.26-5.24 (m, 1H), 5.19-5.15 (m, 1H), 3.97-3.89 (m, 2H), 3.29 (s, 3H), 2.67-2.66 (m, 1H), 2.52 (s, 3H), 1.89-1.84 (m, 2H); MS (ES): m/z 308.4 (M+1).

Example 15

2-chloro-4-((3S,3aS)-5,5-difluoro-3-methoxy-3a,4,5,6-tetrahydro-3H-pyrrolo[1,2-b]pyrazol-2-yl)-3-methylbenzonitrile

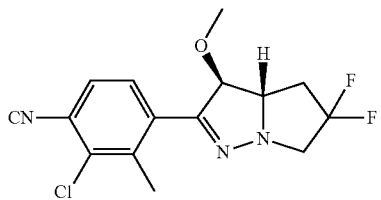

To a stirred solution of compound 2-chloro-4-((3S,3aS)-3-methoxy-5-oxo-3a,4,5,6-tetrahydro-3H-pyrrolo[1,2-b]pyrazol-2-yl)-3-methylbenzonitrile prepared according to example 9 (30 mg, 0.0988 mmol) in DCM (3 mL) at 0° C. was added DAST (0.032 mL, 0.2471 mmol) and stirred for 16 h. Once the starting material had disappeared (monitored by TLC), reaction mixture was diluted with DCM. The organic layer was washed with water, brine, dried over Na$_2$SO$_4$ and concentrated to get the crude title compound which was purified by preparative TLC method using 40% ethylacetate in petroleum ether as eluent.

Wt of the product: 10 mg (32%)
$^1$H NMR (400 MHz, DMSO-d$_6$): δ 7.91 (d, J=8.3 Hz, 1H), 7.71 (d, J=8.3 Hz, 1H), 5.16 (s, 1H), 4.29 (t, J=8.8 Hz, 1H), 3.95 (t, J=8.8 Hz, 1H), 3.77-3.70 (m, 1H), 3.25 (s, 3H), 2.66-2.60 (m, 1H), 2.50 (s, 3H), 1.18-1.10 (m, 1H); IR (KBr): 3439, 2941, 2231, 1589, 1529 cm$^{-1}$; MS (ES): m/z 326 (M+1).

Example 16

2-chloro-4-((3S,3aS,4S)-3-(2-fluoroethoxy)-4-hydroxy-3a,4,5,6-tetrahydro-3H-pyrrolo[1,2-b]pyrazol-2-yl)-3-methylbenzonitrile

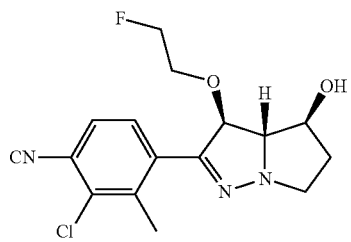

a) 4-((3S,3aR,4S)-4-((tert-butyldimethylsilyl)oxy)-3-(2-((tetrahydro-2H-pyran-2-yl)oxy)ethoxy)-3a,4,5,6-tetrahydro-3H-pyrrolo[1,2-b]pyrazol-2-yl)-2-chloro-3-methylbenzonitrile To a stirred solution of intermediate (IIa) 4-((3S,3aR,4S)-4-(tert-butyldimethylsilyloxy)-3-hydroxy-3a,4,5,6-tetrahydro-3H-pyrrolo[1,2-b]pyrazol-2-yl)-2-chloro-3-methylbenzonitrile (200 mg, 0.493 mmol) in THF (8 mL) at 0° C. was added NaH (24 mg, 0.986 mmol) and stirred for 30 minutes. To this, 2-(2-bromoethoxy)tetrahydro-2H-pyran (124 mg, 0.591 mmol) was added and the reaction mixture was refluxed overnight. Reaction mixture was cooled to room temperature, poured over ice water and extracted with ethyl acetate. Organic layer was washed with water, brine, dried over Na$_2$SO$_4$ and concentrated to get the crude which was purified by column chromatography using 15% ethylacetate in hexane as a solvent.

Wt of the product: 160 mg (61%)
$^1$H NMR (400 MHz, DMSO-d$_6$): δ7.85 (dd, J=2.0 Hz, 8.4 Hz, 1H), 7.76 (dd, J=2.0 Hz, 9.0 Hz, 1H), 5.32 (s, 1H), 4.49 (s, 1H), 4.18-4.14 (m, 1H), 3.68-3.64 (m, 2H), 3.58-3.54 (m, 6H), 2.54 (s, 3H), 1.98-1.85 (m, 1H), 1.68-1.65 (m, 2H), 1.55-1.50 (m, 1H), 1.44-1.39 (m, 4H), 0.89 (s, 9H), 0.11 (s, 6H); MS (ES): m/z 534.1 (M+1).

b) 4-((3S,3aR,4S)-4-((tert-butyldimethylsilyl)oxy)-3-(2-hydroxyethoxy)-3a,4,5,6-tetrahydro-3H-pyrrolo[1,2-b]pyrazol-2-yl)-2-chloro-3-methylbenzonitrile To a stirred solution of 4-((3S,3aR,4S)-4-((tert-butyldimethylsilyl)oxy)-3-(2-((tetrahydro-2H-pyran-2-yl)oxy)ethoxy)-3a,4,5,6-tetrahydro-3H-pyrrolo[1,2-b]pyrazol-2-yl)-2-chloro-3-methylbenzonitrile (160 mg, 0.299 mmol) in methanol (5 mL) at room temperature was added p-toluenesulphonic acid and stirred for 1 h. Once the starting material had disappeared (monitored by TLC) methanol was removed from the reaction mixture and then extracted with EtOAc. Organic layer was washed with water, brine, dried over Na$_2$SO$_4$ and concentrated. Crude product was purified by column chromatography using 15% in ethylacetate in hexane as solvent.

Wt of the product: 80 mg (60%)
$^1$H NMR (400 MHz, CDCl$_3$): δ 7.54 (d, J=8.3 Hz, 1H), 7.49 (d, J=8.3 Hz, 1H), 3.93-3.88 (m, 1H), 3.73-3.63 (m, 5H), 3.58-3.55 (m, 2H), 2.63 (s, 3H), 2.04-1.99 (m, 1H), 1.85-1.82 (m, 2H), 0.91 (s, 9H), 0.10 (s, 6H); MS (ES): m/z 450.2 (M+1).

c) 4-((3S,3aR,4S)-4-((tert-butyldimethylsilyl)oxy)-3-(2-fluoroethoxy)-3a,4,5,6-tetrahydro-3H-pyrrolo[1,2-b]pyrazol-2-yl)-2-chloro-3-methylbenzonitrile To a stirred solution of 4-((3S,3aR,4S)-4-((tert-butyldimethylsilyl)oxy)-3-(2-hydroxyethoxy)-3a,4,5,6-tetrahydro-3H-pyrrolo[1,2-b]pyrazol-2-yl)-2-chloro-3-methylbenzonitrile (30 mg, 0.066 mmol) in DCM (3 mL) at 0° C. was added DAST (0.008 mL, 0.066 mmol) and stirred for 1 h. Once the starting material had disappeared (monitored by TLC), reaction mixture was diluted with DCM and washed with water, brine, dried over Na$_2$SO$_4$ and concentrated to get the crude product which was used in the next step without any purification.

Wt of the product: 30 mg (99%)
$^1$H NMR (400 MHz, CDCl$_3$): δ7.63 (d, J=7.8 Hz, 1H), 7.44 (d, J=7.8 Hz, 1H), 5.27 (s, 1H), 4.03 (d, J=6.4 Hz, 1H), 3.77-3.73 (m, 3H), 3.66 (d, J=5.9 Hz, 1H), 2.62 (s, 3H), 2.13-2.01 (m, 1H), 1.99-1.91 (m, 2H), 1.64-1.61 (m, 2H), 0.98 (s, 9H), 0.17 (s, 6H).

d) 2-chloro-4-((3S,3aS,4S)-3-(2-fluoroethoxy)-4-hydroxy-3a,4,5,6-tetrahydro-3H-pyrrolo[1,2-b]pyrazol-2-yl)-3-methylbenzonitrile To a stirred solution of 4-((3S,3aR,4S)-4-((tert-butyldimethylsilyl)oxy)-3-(2-fluoroethoxy)-3a,4,5,6-tetrahydro-3H- pyrrolo[1,2-b]pyrazol-2-yl)-2-chloro-3-methylbenzonitrile (30 mg, 0.0664 mmol) in THF (4 mL) at 0° C. was added TBAF (0.13 mL, 0.132 mmol, 1M Solution in THF) and stirred for 1 h at room temperature. Once the starting material had disappeared (monitored by TLC), reaction mixture was diluted with ethyl acetate. Organic layer was washed with water, brine, dried over Na$_2$SO$_4$ and concentrated. Crude product was purified by preparative TLC method using 2% methanol in DCM as eluent.

Wt of the product: 7 mg (31%)

$^1$H NMR (400 MHz, CDCl$_3$): δ 7.60-7.50 (m, 2H), 5.24 (s, 1H), 4.59-4.58 (m, 1H), 4.57-4.48 (m, 1H), 4.10 (bs, 1H), 3.76-3.73 (m, 5H), 2.62 (s, 3H), 2.04-2.01 (m, 1H), 1.86-1.85 (m, 2H); MS (ES): m/z 338.2 (M+1).

Example 17

2-chloro-4-((3S,3aS,4S)-3-(cyclopropylmethoxy)-4-hydroxy-3a,4,5,6-tetrahydro-3H-pyrrolo[1,2-b]pyrazol-2-yl)-3-methylbenzonitrile

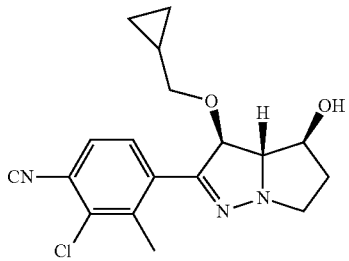

a) 4-((3S,3aR,4S)-4-((tert-butyldimethylsilyl)oxy)-3-(cyclopropylmethoxy)-3a,4,5,6-tetrahydro-3H-pyrrolo[1,2-b]pyrazol-2-yl)-2-chloro-3-methylbenzonitrile To a solution of intermediate (IIa) 4-((3S,3aR,4S)-4-(tert-butyldimethylsilyloxy)-3-hydroxy-3a,4,5,6-tetrahydro-3H-pyrrolo[1,2-b]pyrazol-2-yl)-2-chloro-3-methylbenzonitrile (100 mg, 0.24 mmol) in THF (10 mL) at 0° C. was added NaH (15 mg, 0.36 mmol) and reaction mixture was stirred for 10 minutes. To this bromomethylcyclopropane (0.03 mL, 0.296 mmol) was added and stirred at 65° C. for 12 h. Reaction mixture was cooled to room temperature and poured into ice cold water and extracted with ethyl acetate. Organic layer was washed with water, brine, dried over Na$_2$SO$_4$ and concentrated. Purification of crude product by column chromatography using 5% EtOAc in hexane as eluent provided the title compound.

Wt of the product: 60 mg (54%)

$^1$H NMR (400 MHz, CDCl$_3$): δ7.56-7.51 (m, 2H), 5.08 (s, 1H), 3.90 (q, J=5.8 Hz, 1H), 3.68-3.62 (m, 3H), 3.27-3.23 (m, 2H), 2.62 (s, 3H), 1.99-1.94 (m, 1H), 1.82-1.77 (m, 1H), 1.04-1.00 (m, 1H), 0.90 (s, 9H), 0.54-0.49 (m, 2H), 0.19-0.11 (m, 1H), 0.09 (s, 3H), 0.08 (s, 3H); MS (ES): m/z 459.2 (M+1).

b) 2-chloro-4-((3S,3aS,4S)-3-(cyclopropylmethoxy)-4-hydroxy-3a,4,5,6-tetrahydro-3H-pyrrolo[1,2-b]pyrazol-2-yl)-3-methylbenzonitrile To a stirred solution of 4-((3S,3aR,4S)-4-((tert-butyldimethylsilyl)oxy)-3-(cyclopropylmethoxy)-3a,4,5,6-tetrahydro-3H-pyrrolo[1,2-b]pyrazol-2-yl)-2-chloro-3-methylbenzonitrile (60 mg, 0.13 mmol) in THF (2 mL) at 0° C. was added TBAF (0.26 mL, 0.26 mmol, 1M Solution in THF) and stirred for 1 h at room temperature. Once the starting material had disappeared (monitored by TLC), reaction mixture was diluted with ethyl acetate. Organic layer was washed with water, brine, dried over Na$_2$SO$_4$ and concentrated. Crude product was purified by preparative TLC method (50% EtOAc in hexane).

Wt of the product: 15 mg (33%)

$^1$H NMR (400 MHz, CDCl$_3$): δ7.57-7.52 (m, 2H), 5.19 (s, 1H), 4.12-4.07 (m, 1H), 3.74-3.62 (m, 3H), 3.31-3.27 (m, 2H), 2.62 (s, 3H), 2.02-1.95 (m, 1H), 1.85-1.79 (m, 1H), 1.75 (d, J=4.4 Hz, 1H), 1.04-0.99 (m, 1H), 0.55-0.50 (m, 2H), 0.22-0.12 (m, 2H); MS (ES): m/z 346.1 (M+1).

Example 18

2-chloro-4-((3S,3aS,5S)-5-hydroxy-3-methoxy-3a,4,5,6-tetrahydro-3H-pyrrolo[1,2-b]pyrazol-2-yl)-3-methylbenzonitrile

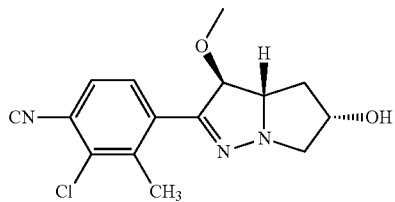

The title compound was obtained by the procedure described in example 2 using 2-chloro-4-((3S,3aS,5R)-5-hydroxy-3-methoxy-3a,4,5,6-tetrahydro-3H-pyrrolo[1,2-b]pyrazol-2-yl)-3-methylbenzonitrile as starting material prepared according to example 8.

$^1$H NMR (400 MHz, DMSO-d$_6$): δ 7.85 (d, J=8.3 Hz, 1H), 7.62 (d, J=8.3 Hz, 1H), 5.12 (s, 1H), 4.69 (d, J=2.5 Hz, 1H), 4.25 (s, 1H), 3.86 (t, J=8.3 Hz, 1H), 3.43 (d, J=12.7 Hz, 1H), 3.22 (s, 3H), 2.58 (s, 3H), 2.31 (d, J=12.7 Hz, 1H), 1.23 (s, 1H), IR (KBr): 3527, 2941, 2872, 2235, 1589 cm$^{-1}$; MS (ES): m/z 305.5 (M+1).

Wt of the product: 8 mg (yield 28%).

Example 19

2-chloro-4-((3S,3aS,5S)-5-iodo-3-methoxy-3a,4,5,6-tetrahydro-3H-pyrrolo[1,2-b]pyrazol-2-yl)-3-methylbenzonitrile

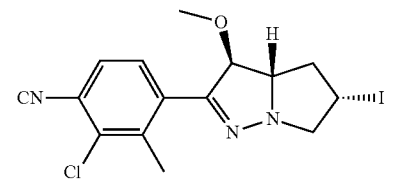

To a stirred solution of 2-chloro-4-((3S,3aS,5R)-5-hydroxy-3-methoxy-3a,4,5,6-tetrahydro-3H-pyrrolo[1,2-b]pyrazol-2-yl)-3-methylbenzonitrile obtained as in example 8 (1.0 g, 3.27 mmol) in THF (40 mL) at 0° C. were added DIAD (0.8 mL, 3.96 mmol), PPh$_3$ (1.28 g, 4.87 mmol) and methyl Iodide (0.25 mL, 3.92 mmol) and the reaction mixture was stirred at room temperature for 24 h. Once the starting material had disappeared (monitored by TLC), reaction mixture was diluted with ethyl acetate, water and extracted. Organic layer was washed with water, brine, dried over Na$_2$SO$_4$ and concentrated. Purification by column chromatography (silica gel, 5% acetone in hexane) provided the title compound (0.8 g, 59%)

$^1$H NMR (400 MHz, CDCl$_3$): δ 7.54 (d, J=8.4 Hz, 1H), 7.49 (d, J=8.3 Hz, 1H), 4.89 (s, 1H), 4.23-4.20 (m, 1H), 4.18-4.12 (m, 1H), 3.98-3.94 (m, 1H), 3.71-3.65 (m, 1H), 3.31 (s, 3H), 2.61 (s, 3H), 2.49-2.42 (m, 1H), 2.18-2.11 (m, 1H); MS (ES): m/z 416.1 (M+1).

Example 20

2-chloro-4-((3S,3aS,4S)-3,4-dimethoxy-3a,4,5,6-tetrahydro-3H-pyrrolo[1,2-b]pyrazol-2-yl)-3-methylbenzonitrile

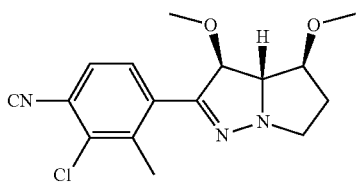

To a stirred solution of 2-chloro-4-((3S,3aS,4S)-4-hydroxy-3-methoxy-3a,4,5,6-tetrahydro-3H-pyrrolo[1,2-b]pyrazol-2-yl)-3-methylbenzonitrile as obtained in example 1 (50 mg, 0.16 mmol) in THF (3 mL) at 0° C. was added sodium hydride (13 mg, 0.33 mmol) for 10 min, followed by the addition of methyl iodide (0.015 mL, 0.245 mmol). The reaction mixture was stirred at room temperature for 2 h. Once the starting material had disappeared (monitored by TLC) reaction mixture was quenched with saturated ammonium chloride and extracted with ethyl acetate, organic layer was washed with water, brine, dried over Na$_2$SO$_4$ and concentrated. Purification by column chromatography (silica gel, 30% EtOAc in Hexane) provided the title compound (10 mg, 20%).

$^1$H NMR (400 MHz, CDCl$_3$): δ 7.55-7.49 (m, 2H), 5.08 (d, J=1.0 Hz, 1H), 5.50 (d, J=1.0 Hz, 1H), 3.77-3.73 (m, 2H), 3.66-3.65 (m, 1H), 3.59-3.53 (m, 1H), 3.39 (s, 3H), 3.32 (s, 3H), 2.61 (s, 3H), 1.88-1.84 (m, 2H); MS (ES): m/z 320.2 (M+1).

Example 21

2-chloro-4-((3S,3aS,4S)-4-hydroxy-3-(2-methoxyethoxy)-3a,4,5,6-tetrahydro-3H-pyrrolo[1,2-b]pyrazol-2-yl)-3-methylbenzonitrile

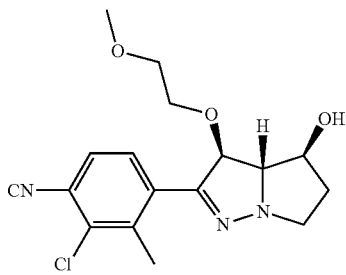

a) 4-((3S,3aR,4S)-4-((tert-butyldimethylsilyl)oxy)-3-(2-methoxyethoxy)-3a,4,5,6-tetrahydro-3H-pyrrolo[1,2-b]pyrazol-2-yl)-2-chloro-3-methylbenzonitrile To a suspension of sodium hydride (99 mg, 2.5 mmol) in THF (5 mL) at 0° C. was added a solution of intermediate (IIa) (500 mg, 1.2 mmol) in THF (10 mL) and stirred for 10 min, followed by the addition of 1-bromo-2-methoxyethane (0.14 mL, 1.5 mmol). The reaction mixture was stirred at 70° C. for 5 h. Once the starting material had disappeared (monitored by TLC), the reaction was cooled and quenched with saturated ammonium chloride and extracted with ethyl acetate, organic layer was washed with water, brine, dried over Na$_2$SO$_4$ and concentrated. Purification by column chromatography (silica gel, 10% EtOAc in Hexane) provided the title compound (500 mg, 87%).

$^1$H NMR (400 MHz, CDCl$_3$): δ 7.59 (d, J=7.8 Hz, 1H), 7.53 (d, J=8.3 Hz, 1H), 5.15 (d, J=1.0 Hz, 1H), 3.91-3.89 (m, 1H), 3.68-3.64 (m, 3H), 3.58-3.50 (m, 2H), 3.49-3.47 (m, 2H), 3.32 (s, 3H), 2.62 (s, 3H), 1.96-1.94 (m, 1H), 1.81-1.80 (m, 1H), 0.91 (s, 9H), 0.09 (d, J=5.3 Hz, 6H); MS (ES): m/z 464.1 (M+1).

b) 2-chloro-4-((3S,3aS,4S)-4-hydroxy-3-(2-methoxyethoxy)-3a,4,5,6-tetrahydro-3H-pyrrolo[1,2-b]pyrazol-2-yl)-3-methylbenzonitrile The title compound was synthesized using the same procedure which was followed for example 3.

$^1$H NMR (400 MHz, CDCl$_3$): δ 7.58-7.52 (m, 2H), 5.25 (d, J=1.0 Hz, 1H), 4.10-4.00 (m, 1H), 3.72-3.65 (m, 4H), 3.57-3.51 (m, 3H), 3.34 (s, 3H), 2.61 (s, 3H), 2.05-2.00 (m, 2H), 1.85-1.80 (m, 1H); IR (KBr): 3304, 3219, 2922, 2881, 2852, 2231, 1591 cm$^{-1}$; MS (ES): m/z 350.2 (M+1).

Example 22

2-chloro-4-((3S,3aR,4R)-4-fluoro-3-(2-methoxyethoxy)-3a,4,5,6-tetrahydro-3H-pyrrolo[1,2-b]pyrazol-2-yl)-3-methylbenzonitrile

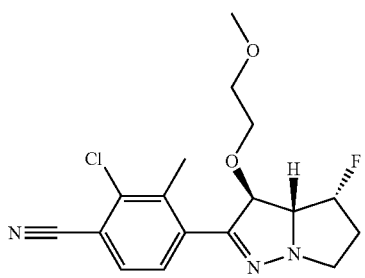 [SMILES: COCCO[C@@H]1C(c2ccc(C#N)c(Cl)c2C)=NN2CC[C@@H](F)[C@@H]12]

To a stirred solution of 2-chloro-4-((3S,3aS,4S)-4-hydroxy-3-(2-methoxyethoxy)-3a,4,5,6-tetrahydro-3H-pyrrolo[1,2-b]pyrazol-2-yl)-3-methylbenzonitrile obtained in example 21 (400 mg, 1.14 mmol) in DCM (10 mL) at 0° C. was added DAST (0.18 mL, 1.34 mmol) and stirred at room temperature for 1 h. Once the starting material had disappeared (monitored by TLC), the reaction mixture was diluted with DCM, water and extracted, organic layer was washed with water, brine, dried over Na$_2$SO$_4$ and concentrated. Purification by column chromatography (silica gel, 30% EtOAc in Hexane) provided the title compound (215 mg, 53%).

¹H NMR (400 MHz, CDCl₃): δ 7.57-7.51 (m, 2H), 5.45 (d, J=1.5 Hz, 1H), 5.33-5.30 & 5.19-5.17 (2 m, 1H), 3.92-3.91 & 3.87-3.83 (2 m, 1H), 3.70-3.65 (m, 3H), 3.61-3.45 (m, 4H), 3.33 (s, 3H), 2.59 (s, 3H), 2.32-2.20 (m, 1H), 2.19-2.11 (m, 1H); MS (ES): m/z 352.3 (M+1).

Example 23

2-chloro-4-((3S,3aR,4R)-4-fluoro-3-(2-fluoroethoxy)-3a,4,5,6-tetrahydro-3H-pyrrolo[1,2-b]pyrazol-2-yl)-3-methylbenzonitrile

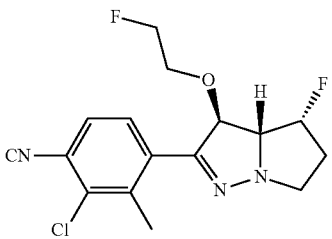

To a stirred solution of 2-chloro-4-((3S,3aS,4S)-3-(2-fluoroethoxy)-4-hydroxy-3a,4,5,6-tetrahydro-3H-pyrrolo[1,2-b]pyrazol-2-yl)-3-methylbenzonitrile obtained in example 16 (120 mg, 0.36 mmol) in DCM (5 mL) at 0° C. was added DAST (0.05 mL, 0.43 mmol) and stirred at room temperature for 14 h. Once the starting material had disappeared (monitored by TLC) reaction mixture was diluted with DCM, water and extracted. Organic layer was washed with water, brine, dried over Na₂SO₄ and concentrated. Purification by column chromatography (silica gel, 50% EtOAc in Hexane) provided the title compound (60 mg, 50%).
¹H NMR (400 MHz, CDCl₃): δ 7.57-7.50 (m, 2H), 5.44 (d, J=1.5 Hz, 1H), 5.35-5.33 & 5.21-5.19 (2 m, 1H), 4.56-4.54 (m, 1H), 4.44-4.42 (m, 1H), 3.87 (dd, J=2.4 Hz, J=30.8 Hz, 1H), 3.74-3.58 (m, 4H), 2.59 (s, 3H), 2.33-2.12 (m, 2H); MS (ES): m/z 340.2 (M+1).

Example 24

2-chloro-4-((3S,3aS)-5,5-difluoro-3-(2-methoxyethoxy)-3a,4,5,6-tetrahydro-3H-pyrrolo[1,2-b]pyrazol-2-yl)-3-methylbenzonitrile

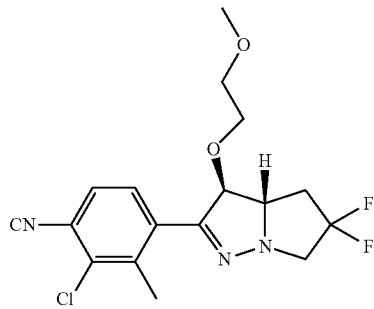

a) 2-chloro-4-((3S,3aS,5R)-5-hydroxy-3-(2-methoxyethoxy)-3a,4,5,6-tetrahydro-3H-pyrrolo[1,2-b]pyrazol-2-yl)-3-methylbenzonitrile The title compound was synthesised using the same procedure which was followed for example 21 starting with intermediate (IIb).
MS (ES): m/z 348.2 (M−1)

b) 2-chloro-4-((3S,3aS)-3-(2-methoxyethoxy)-5-oxo-3a,4,5,6-tetrahydro-3H-pyrrolo[1,2-b]pyrazol-2-yl)-3-methylbenzonitrile To a solution of 2-chloro-4-((3S,3aS,5R)-5-hydroxy-3-(2-methoxyethoxy)-3a,4,5,6-tetrahydro-3H-pyrrolo[1,2-b]pyrazol-2-yl)-3-methylbenzonitrile (50 mg, 0.143 mmol) in DCM (5 mL) at 0° C. was added Dessmartin reagent (121 mg, 0.286 mmol) and reaction mixture was stirred at room temperature for 16 h. Once the starting material had disappeared (monitored by TLC), reaction mixture was diluted with ethyl acetate, water and extracted. Organic layer was washed with saturated NaHCO₃ solution, water, and brine then dried over Na₂SO₄ and concentrated. Purification by column chromatography (silica gel, 1% MeOH in DCM) provided the title compound (36 mg, 73%).
MS (ES): m/z 346.3 (M−1)

c) 2-chloro-4-((3S,3aS)-5,5-difluoro-3-(2-methoxyethoxy)-3a,4,5,6-tetrahydro-3H-pyrrolo[1,2-b]pyrazol-2-yl)-3-methylbenzonitrile To a solution of compound 2-chloro-4-((3S,3aS)-3-(2-methoxyethoxy)-5-oxo-3a,4,5,6-tetrahydro-3H-pyrrolo[1,2-b]pyrazol-2-yl)-3-methylbenzonitrile (30 mg, 0.086 mmol) in DCM (4 mL) at 0° C. was added DAST (0.03 mL, 0.215 mmol) and the reaction mixture was stirred at room temperature for 16 h. Once the starting material was disappeared (monitored by TLC), reaction mixture was diluted with ethyl acetate, water and extracted. Organic layer was washed with Saturated NaHCO₃ solution, water, and brine then dried over Na₂SO₄ and concentrated. Purification by column chromatography (silica gel, 30% EtOAc in hexane) provided the title compound (3 mg, 10%).
¹H NMR (400 MHz, CDCl₃): δ 7.60-7.55 (m, 2H), 5.06 (bs, 1H), 4.23-4.06 (m, 2H), 3.72-3.49 (m, 5H), 3.34 (s, 3H), 2.63 (s, 3H), 2.54 (bs, 1H), 2.06 (bs, 1H);
MS (ES): m/z 368.3 (M−1).

Example 25

2-chloro-4-((3S,3aS,4R,5S)-4,5-dihydroxy-3-methoxy-3a,4,5,6-tetrahydro-3H-pyrrolo[1,2-b]pyrazol-2-yl)-3-methylbenzonitrile

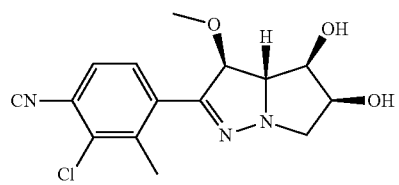

a) 2-chloro-4-((3S,3aS))-3-methoxy-3a,6-dihydro-3H-pyrrolo[1,2-b]pyrazol-2-yl)-3-methylbenzonitrile To a stirred solution of 2-chloro-4-((3S,3aS,5S)-5-iodo-3-methoxy-3a,4,5,6-tetrahydro-3H-pyrrolo[1,2-b]pyrazol-2-yl)-3-methylbenzonitrile (obtainable as described in example 19) (800 mg, 1.92 mmol) in toluene (15 mL) at room temperature was added DBU (0.35 mL) and the reaction mixture was stirred at 85° C. for 3 h. Once the starting material was disappeared (monitored by TLC), reaction mixture was diluted with ethyl acetate, water and extracted. Organic layer was washed with water, brine, dried over Na$_2$SO$_4$ and concentrated. Purification by column chromatography (silica gel, 15% EtOAc in Hexane) provided the title compound (460 mg, 83%).

$^1$H NMR (400 MHz, CDCl$_3$): δ 7.53 (d, J=8.3 Hz, 1H), 7.50 (d, J=8.3 Hz, 1H), 5.90 (s, 1H), 5.72 (s, 1H), 4.98 (s, 1H), 4.53 (s, 1H), 4.33-4.13 (m, 2H), 3.31 (s, 3H), 2.57 (s, 3H); MS (ES): m/z 288.2 (M+1).

b) 2-chloro-4-((3S,3aS,4R,5S)-4,5-dihydroxy-3-methoxy-3a,4,5,6-tetrahydro-3H-pyrrolo[1,2-b]pyrazol-2-yl)-3-methylbenzonitrile To a stirred solution of 2-chloro-4-((3S,3aS))-3-methoxy-3a,6-dihydro-3H-pyrrolo[1,2-b]pyrazol-2-yl)-3-methylbenzonitrile (460 mg, 1.6 mmol) in acetone (5 mL) was added NMO (0.7 mL, 50% solution in water, 2.4 mmol,) and the reaction mixture was cooled to 0° C. followed by the addition of OsO$_4$ (0.2 mL, 2% solution in toluene, 0.016 mmol,). The reaction mixture was stirred at room temperature for 5 h. Once the starting material had disappeared (monitored by TLC), reaction mixture was quenched with saturated sodium-metabisulfite solution and extracted with ethyl acetate. Organic layer was washed with water, brine, dried over Na$_2$SO$_4$ and concentrated. Purification by column chromatography (silica gel, 2% MeOH in DCM) provided the title compound (175 mg, 34%).

$^1$H NMR (400 MHz, DMSO-d$_6$): δ 7.84 (d, J=8.3 Hz, 1H), 7.57 (d, J=8.3 Hz, 1H), 5.39 (d, J=2.5 Hz, 1H), 5.01 (d, J=4.0 Hz, 1H), 4.90 (d, J=5.9 Hz, 1H), 4.18-4.15 (m, 1H), 4.05-4.02 (m, 1H), 3.77-3.76 (m, 1H), 3.56-3.52 (m, 1H), 3.17 (s, 3H), 2.55 (s, 3H); MS (ES): m/z 322.1 (M+1).

Example 32

Biological Activity of Compounds of Formula I

The compounds of the Examples hereinbefore show the following EC$_{50}$ values in Test 1 described hereinbefore.

Materials and Methods:

C2C12 cells were obtained from ATCC (Cat # CRL-1772) and maintained in DMEM modified to contain 4 mM L-glutamine, 4.5 g/L glucose, 1 mM sodium pyruvate and 1.5 g/L sodium bicarbonate and 10% FBS.

96-well tissue culture treated plates—clear flat bottom BD Cat #353072

96-well plate white Greiner Cat #655075
Dihydro Testosterone (DHT) TCI Cat # A0462
OptiMEM Gibco Cat #31985
Lipofectamine 2000 Invitrogen Cat #11668-019
AR-FL in pcDNA 3.1(+) and 2XIDR17 in pGL4.26 plasmids prepared using Genelute plasmid miniprep kit from Sigma Cat # PLED35
Steadyglow Luciferase assay system Promega Cat # E2550

Assay Protocol:

C2C12 cells were seeded in a 96-well plate in DMEM (Dulbecco's Modified Eagle Medium) without phenol red and containing 10% CS-FBS (Charcoal-stripped Fetal Bovine Serum) at 8000 cells/well.

The next day, cells were transfected with an equimolar ratio of (Androgen Receptor-Full length) AR-FL and 2XIDR17-Luciferase at a total plasmid concentration of 200 ng/well using Lipofectamine 2000 following manufacturer's protocol.

For the transfection, 83 ng of AR-FL and 117 ng of 2XIDR17-Luciferase were in 12.5 μl of OptiMEM—Mix A. 0.4 μl of Lipofectamine 2000 was added to 12.5 μl of OptiMEM and incubated for 5 min at room temperature—Mix B. The two mixes A and B were mixed and incubated at room temperature for an additional fifteen minutes. An additional 50 μl of OptiMEM was added, gently mixed and this mixture was added to the cells in the 96-well plate. The above quantities are requirements per well of a 96-well plate. Master mixes were made for the entire plate, with proportional quantity of reagents being used.

5 h after transfection, compounds were added to the wells in DMEM without phenol red and containing 10% CS-FBS, maintaining a final DMSO concentration of 0.5%. A typical dose response curve starts at 10 μM and includes a 7-point, log dilution, done in triplicates.

After overnight incubation with the compounds, 100 ul of working solution of Steadyglow reagent was added to the wells.

The plates were placed in a shaker for 15 min at the end of which the lysate containing luciferase was transferred to a white flat-bottom plate and read under a luminescence setting in Victor.

Background subtracted counts (Luminescence from DMSO control wells is considered the background) are used to calculate percentage activity, expressed relative to activity with 1 μM (Dihydrotestosterone) DHT (at least two sets of triplicates for 1 μM DHT are included per plate).

Data Fitting:

The EC$_{50}$ curves for the compounds for 8 compound concentrations were fitted by the respective function using non-linear least-squares regression in Graphpad Prism 4.0 (Graphpad Software, San Diego, Calif., USA).

Examples 26 to 31 were synthesised in analogous manner to the examples described above.

TABLE 1

| Example number | Chemical structure | Biological activity (C2C12 cell) EC50 (nM) |
|---|---|---|
| 1 | 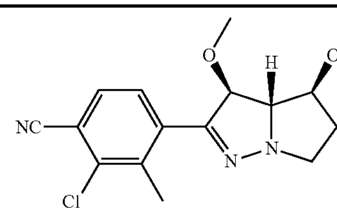 | 0.5 |
| 2 | 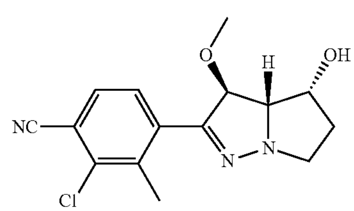 [SMILES: CO[C@@H]1C(c2ccc(C#N)c(Cl)c2C)=NN2CC[C@@H](O)[C@@H]12] | 0.6 |
| 3 | 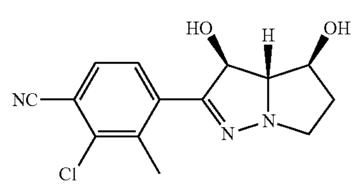 [SMILES: Cc1c(C2=NN3CC[C@H](O)[C@H]3[C@@H]2O)ccc(C#N)c1Cl] | 821 |

TABLE 1-continued

| Example number | Chemical structure | Biological activity (C2C12 cell) EC50 (nM) |
|---|---|---|
| 4 | (structure) | 5/32* |
| 5 | (structure) | 1.2 |
| 6 | (structure) | 0.6 |
| 7 | (structure) | 4 |
| 8 | (structure) | 6.7 |
| 9 | (structure) | 10.5 |
| 10 | (structure) | 4/2* |
| 11 | (structure) | 24/33* |
| 12 | (structure) | 0.1 |
| 13 | (structure) | 1.3 |
| 14 | (structure) | 1.7 |
| 15 | (structure) | 0.1 |
| 16 | (structure) | 2 |
| 17 | (structure) | 91/100* |
| 18 | (structure) | ** |

TABLE 1-continued

| Example number | Chemical structure | Biological activity (C2C12 cell) EC50 (nM) |
|---|---|---|
| 19 | 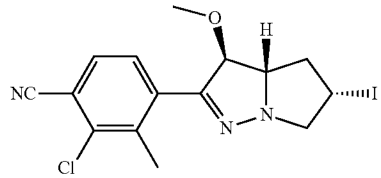 [SMILES: CO[C@@H]1C(c2ccc(C#N)c(Cl)c2C)=NN2C[C@@H](I)C[C@@H]12] | 7 |
| 20 | 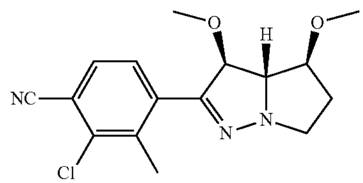 | 7.1 |
| 21 | 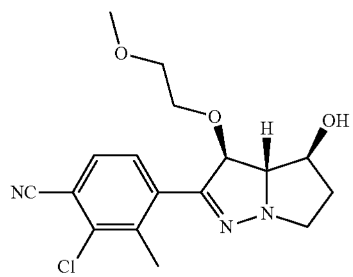 [SMILES: COCCO[C@@H]1C(c2ccc(C#N)c(Cl)c2C)=NN2CC[C@H](O)[C@@H]12] | 0.93 |
| 22 | 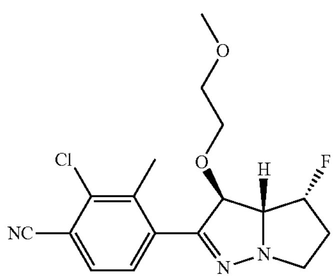 [SMILES: COCCO[C@@H]1C(c2ccc(C#N)c(Cl)c2C)=NN2CC[C@@H](F)[C@@H]12] | 0.98 |
| 23 | 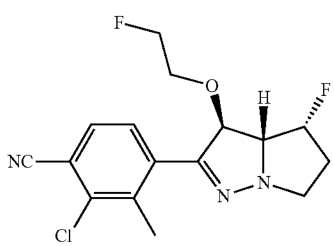 [SMILES: Cc1c(C2=NN3CC[C@@H](F)[C@H]3[C@@H]2OCCF)ccc(C#N)c1Cl] | 0.41 |
| 24 | 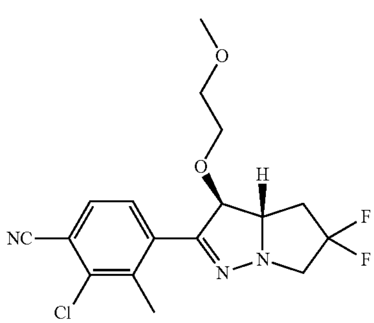 [SMILES: COCCO[C@@H]1C(c2ccc(C#N)c(Cl)c2C)=NN2CC(F)(F)C[C@@H]12] | 5.6 |
| 25 | 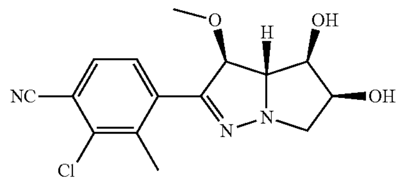 [SMILES: CO[C@@H]1C(c2ccc(C#N)c(Cl)c2C)=NN2C[C@H](O)[C@H](O)[C@@H]12] | 51.2 |
| 26 | 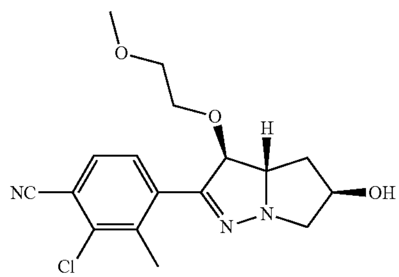 [SMILES: COCCO[C@@H]1C(c2ccc(C#N)c(Cl)c2C)=NN2C[C@H](O)C[C@@H]12] | 157.7 |
| 27 | 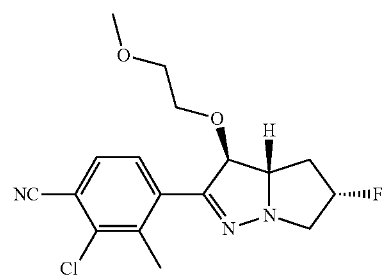 [SMILES: COCCO[C@@H]1C(c2ccc(C#N)c(Cl)c2C)=NN2C[C@@H](F)C[C@@H]12] | 65.8 |
| 28 | 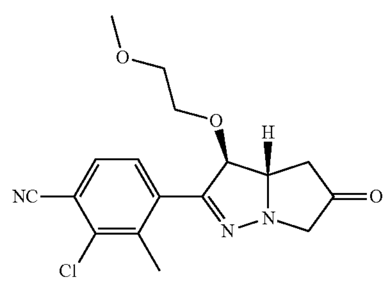 [SMILES: COCCO[C@@H]1C(c2ccc(C#N)c(Cl)c2C)=NN2CC(=O)C[C@@H]12] | 174.6 |
| 29 | 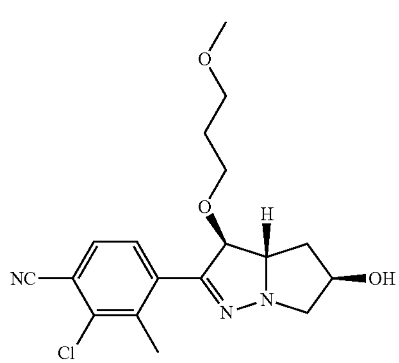 [SMILES: COCCCO[C@@H]1C(c2ccc(C#N)c(Cl)c2C)=NN2C[C@H](O)C[C@@H]12] | 40 |

TABLE 1-continued

| Example number | Chemical structure | Biological activity (C2C12 cell) EC50 (nM) |
|---|---|---|
| 30 | 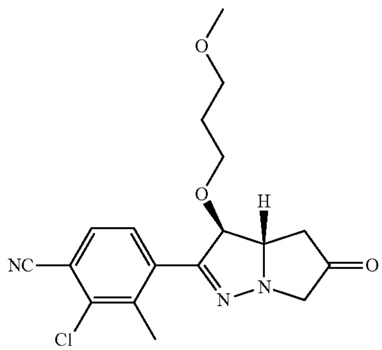 [SMILES: COCCCO[C@@H]1C(c2ccc(C#N)c(Cl)c2C)=NN2CC(=O)C[C@@H]12] | 56 |
| 31 | 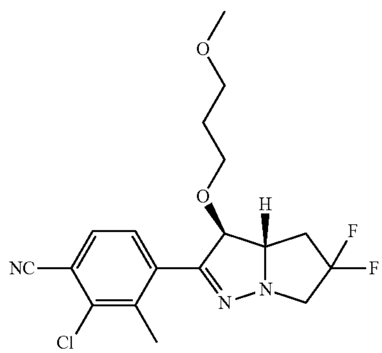 [SMILES: COCCCO[C@@H]1C(c2ccc(C#N)c(Cl)c2C)=NN2CC(F)(F)C[C@@H]12] | 11.44 |

*% Biological activity (C2C12 cell) 100 nM/5 μM
** at 5 μM concentration, <10% activity

Example 33

In Vivo Modified Hershberger Assay Comparing Compounds of Formula I with Testosterone and Ostarine Efficacy of Testosterone Propionate, Ostarine, Compounds of Examples 1 and 5 in Modified Hershberger Assay in Male Wistar Rats Evaluation of Testosterone Propionate, Ostarine, examples 1 and 5 in modified Hershberger assay in male wistar rats was conducted at the Department of Preclinical Biology, Aurigene Discovery Technologies Ltd., Bangalore, India.

All rats from respective treatment groups survived during the course of the study period of 14 days. No significant alterations were observed in any of the in-life parameters (clinical signs, body weight, and food consumption) during the course of study period.

The 14 days treatment of Ostarine, compounds of examples 1 and 5 to orchidectomized male rats showed dose dependent selective increase in weights of levator ani compared to prostate (cf. FIGS. 1 and 2). Testosterone Propionate did not show any selectivity on levator ani versus prostate.

The clinical pathology parameters viz. hematology and clinical chemistry showed no adverse changes while dose dependent decrease was observed for luteinizing hormone (LH) levels for all test articles in comparison to ORX animals. The dose dependent increase of plasma drug concentration of Ostarine, compounds of examples 1 and 5 was observed on day 15, 3 hours after last dose for the both the test articles.

In conclusion, the 14 days treatment of Ostarine, compound of examples 1 and 5 to orchidectomized male rats showed dose dependent selective increase in levator ani weight compared to prostate weight with concurrent decrease of LH levels. Based on this it could be concluded that both test articles are having selective androgen receptor agonist activity in muscle compared to prostate. No test article related adverse toxic findings were observed during the course of study period of 14 days treatment with respect to in life data parameters like clinical signs, body weight, food consumption, hematology & clinical chemistry and the macroscopic findings during necropsy.

The following are further embodiments of the invention:

Embodiment 1

A compound of formula (I) in free form or in pharmaceutically acceptable salt form,

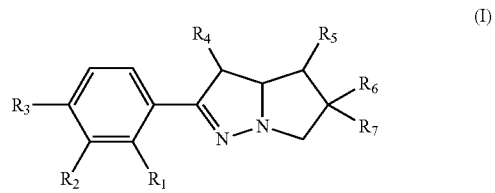

(I)

wherein $R_1$ is $C_1$-$C_3$alkyl;

$R_2$ is halogen;

$R_3$ is cyano;

$R_4$ is selected from amino, halogen, hydroxy, $C_1$-$C_3$alkyl, halogen-$C_1$-$C_3$alkyl, hydroxy-$C_1$-$C_3$alkyl, $C_3$-$C_6$cycloalkyl, $C_1$-$C_3$alkoxy, halogen-$C_1$-$C_3$alkoxy, $C_1$-$C_3$alkoxy-$C_1$-$C_3$alkoxy, $C_3$-$C_6$cycloalkyl-$C_1$-$C_3$alkoxy, $C_3$-$C_6$cycloalkoxy; or $R_4$ is selected from a (=O), (=S) or (=N($R_8$)) group;

$R_5$ is selected from hydrogen, amino, halogen, hydroxy, $C_1$-$C_3$alkyl, halogen-$C_1$-$C_3$alkyl, hydroxy-$C_1$-$C_3$alkyl, $C_3$-$C_6$cycloalkyl, $C_1$-$C_3$alkoxy, halogen-$C_1$-$C_3$alkoxy, $C_3$-$C_6$cycloalkoxy; or $R_5$ is selected from a (=O), (=S) or (=N($R'_8$)) group;

$R_6$ is selected from hydrogen, amino, halogen, hydroxy, $C_1$-$C_3$alkyl, halogen-$C_1$-$C_3$alkyl, $C_3$-$C_6$cycloalkyl, $C_1$-$C_3$alkoxy, halogen-$C_1$-$C_3$alkoxy, $C_3$-$C_6$cycloalkoxy;

$R_7$ is selected from hydrogen, halogen, halogen-$C_1$-$C_3$alkyl;

or $R_6$ and $R_7$ together with the carbon to which they are attached form a —C(=O)— or —C(=S)— group;

$R_8$ and $R'_8$ are independently selected from hydrogen, hydroxy;

provided $R_5$, $R_6$, and $R_7$ are not all hydrogen.

Embodiment 2

A compound of formula (Ia) according to embodiment 1 in free from or in pharmaceutically acceptable salt form

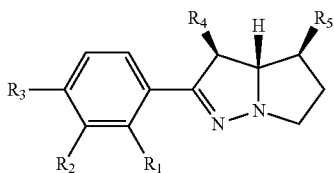

(Ia)

wherein $R_1$, $R_2$, $R_3$, $R_4$ and $R_5$ are as defined in claim 1, wherein $R_5$ is not hydrogen.

Embodiment 3

A compound of formula (Ib) according to embodiment 1 in free from or in pharmaceutically acceptable salt form

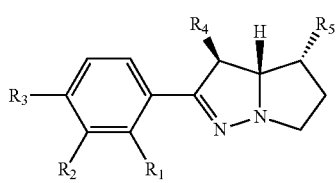

(Ib)

wherein $R_1$, $R_2$, $R_3$, $R_4$ and $R_5$ are as defined in claim 1, wherein $R_5$ is not hydrogen.

Embodiment 4

A compound of formula (Ic) according to embodiment 1 in free from or in pharmaceutically acceptable salt form

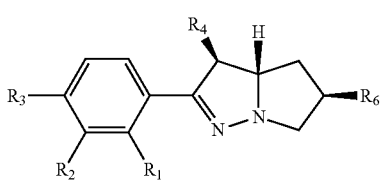

(Ic)

wherein $R_1$, $R_2$, $R_3$, $R_4$ and $R_6$ are as defined in claim 1, wherein $R_6$ is not hydrogen.

Embodiment 5

A compound of formula (Id) according to embodiment 1 in free form or in pharmaceutically acceptable salt form

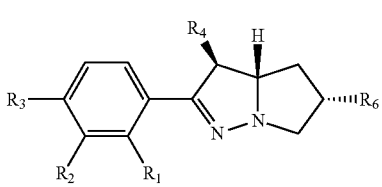

(Id)

wherein $R_1$, $R_2$, $R_3$, $R_4$ and $R_6$ are as defined in claim 1, wherein $R_6$ is not hydrogen.

Embodiment 6

A compound according to any of embodiments 1 to 5 in free form or in pharmaceutically acceptable salt form, wherein
$R_1$ is methyl; $R_2$ is chloro; $R_3$ is cyano;

Embodiment 7

A compound according to any of embodiments 1 to 6 in free form or in pharmaceutically acceptable salt form, wherein $R_4$ is selected from hydroxy, $C_1$-$C_3$alkoxy.

Embodiment 8

A compound according to any of embodiments 1 to 7 in free form or in pharmaceutically acceptable salt form, wherein $R_5$ if present is selected from halogen, hydroxy.

Embodiment 9

A compound according to any of embodiments 1 to 8 in free form or in pharmaceutically acceptable salt form, wherein $R_6$ if present is selected from halogen, hydroxy.

Embodiment 10

A compound according to any of embodiments 1 to 9 in free form or in pharmaceutically acceptable salt form, wherein $R_7$ if present is hydrogen.

Embodiment 11

A compound according to embodiment 1 in free form or in pharmaceutically acceptable salt form, which is selected from
2-chloro-4-(4-hydroxy-3-methoxy-3a,4,5,6-tetrahydro-3H-pyrrolo[1,2-b]pyrazol-2-yl)-3-methylbenzonitrile;
2-chloro-4-(3,4-dihydroxy-3a,4,5,6-tetrahydro-3H-pyrrolo[1,2-b]pyrazol-2-yl)-3-methylbenzonitrile;
2-chloro-4-(3-ethoxy-4-hydroxy-3a,4,5,6-tetrahydro-3H-pyrrolo[1,2-b]pyrazol-2-yl)-3-methylbenzonitrile;
2-chloro-4-(4-hydroxy-3-isopropoxy-3a,4,5,6-tetrahydro-3H-pyrrolo[1,2-b]pyrazol-2-yl)-3-methylbenzonitrile;
2-chloro-4-(5-hydroxy-3-methoxy-3a,4,5,6-tetrahydro-3H-pyrrolo[1,2-b]pyrazol-2-yl)-3-methylbenzonitrile;
2-chloro-4-(3-methoxy-5-oxo-3a,4,5,6-tetrahydro-3H-pyrrolo[1,2-b]pyrazol-2-yl)-3-methylbenzonitrile;
2-chloro-4-(3,5-dihydroxy-3a,4,5,6-tetrahydro-3H-pyrrolo[1,2-b]pyrazol-2-yl)-3-methylbenzonitrile;
2-chloro-4-(5-hydroxy-3-methoxy-5-(trifluoromethyl)-3a,4,5,6-tetrahydro-3H-pyrrolo[1,2-b]pyrazol-2-yl)-3-methylbenzonitrile;
2-chloro-4-(4-fluoro-3-methoxy-3a,4,5,6-tetrahydro-3H-pyrrolo[1,2-b]pyrazol-2-yl)-3-methylbenzonitrile;
2-chloro-4-(5-fluoro-3-methoxy-3a,4,5,6-tetrahydro-3H-pyrrolo[1,2-b]pyrazol-2-yl)-3-methylbenzonitrile;
2-chloro-4-(5,5-difluoro-3-methoxy-3a,4,5,6-tetrahydro-3H-pyrrolo[1,2-b]pyrazol-2-yl)-3-methylbenzonitrile;
2-chloro-4-(3-(2-fluoroethoxy)-4-hydroxy-3a,4,5,6-tetrahydro-3H-pyrrolo[1,2-b]pyrazol-2-yl)-3-methylbenzonitrile;
2-chloro-4-(3-(cyclopropylmethoxy)-4-hydroxy-3a,4,5,6-tetrahydro-3H-pyrrolo[1,2-b]pyrazol-2-yl)-3-methylbenzonitrile;
2-chloro-4-(5-iodo-3-methoxy-3a,4,5,6-tetrahydro-3H-pyrrolo[1,2-b]pyrazol-2-yl)-3-methylbenzonitrile;

2-chloro-4-(3,4-dimethoxy-3a,4,5,6-tetrahydro-3H-pyrrolo [1,2-b]pyrazol-2-yl)-3-methylbenzonitrile;
2-chloro-4-(4-hydroxy-3-(2-methoxyethoxy)-3a,4,5,6-tetrahydro-3H-pyrrolo[1,2-b]pyrazol-2-yl)-3-methylbenzonitrile;
2-chloro-4-(4-fluoro-3-(2-methoxyethoxy)-3a,4,5,6-tetrahydro-3H-pyrrolo[1,2-b]pyrazol-2-yl)-3-methylbenzonitrile;
2-chloro-4-(4-fluoro-3-(2-fluoroethoxy)-3a,4,5,6-tetrahydro-3H-pyrrolo[1,2-b]pyrazol-2-yl)-3-methylbenzonitrile and
2-chloro-4-(5,5-difluoro-3-(2-methoxyethoxy)-3a,4,5,6-tetrahydro-3H-pyrrolo[1,2-b]pyrazol-2-yl)-3-methylbenzonitrile.

Embodiment 12

A compound according to embodiment 11 in free form or in pharmaceutically acceptable salt form which is selected from
2-chloro-4-((3S,3aS,4S)-4-hydroxy-3-methoxy-3a,4,5,6-tetrahydro-3H-pyrrolo[1,2-b]pyrazol-2-yl)-3-methylbenzonitrile;
2-chloro-4-((3S,3aS,4R)-4-hydroxy-3-methoxy-3a,4,5,6-tetrahydro-3H-pyrrolo[1,2-b]pyrazol-2-yl)-3-methylbenzonitrile;
2-chloro-4-((3S,3aS,4S)-3-ethoxy-4-hydroxy-3a,4,5,6-tetrahydro-3H-pyrrolo[1,2-b]pyrazol-2-yl)-3-methylbenzonitrile;
2-chloro-4-((3S,3aS,4R)-3-ethoxy-4-hydroxy-3a,4,5,6-tetrahydro-3H-pyrrolo[1,2-b]pyrazol-2-yl)-3-methylbenzonitrile;
2-chloro-4-((3S,3aR,4R)-4-fluoro-3-methoxy-3a,4,5,6-tetrahydro-3H-pyrrolo[1,2-b]pyrazol-2-yl)-3-methylbenzonitrile;
2-chloro-4-((3S,3aR,4S)-4-fluoro-3-methoxy-3a,4,5,6-tetrahydro-3H-pyrrolo[1,2-b]pyrazol-2-yl)-3-methylbenzonitrile;
2-chloro-4-((3S,3aS)-5,5-difluoro-3-methoxy-3a,4,5,6-tetrahydro-3H-pyrrolo[1,2-b]pyrazol-2-yl)-3-methylbenzonitrile;
2-chloro-4-((3S,3aS,5S)-5-iodo-3-methoxy-3a,4,5,6-tetrahydro-3H-pyrrolo[1,2-b]pyrazol-2-yl)-3-methylbenzonitrile;
2-chloro-4-((3S,3aS,4S)-3,4-dimethoxy-3a,4,5,6-tetrahydro-3H-pyrrolo[1,2-b]pyrazol-2-yl)-3-methylbenzonitrile;
2-chloro-4-((3S,3aS,4S)-4-hydroxy-3-(2-methoxyethoxy)-3a,4,5,6-tetrahydro-3H-pyrrolo[1,2-b]pyrazol-2-yl)-3-methylbenzonitrile;
2-chloro-4-((3S,3aR,4R)-4-fluoro-3-(2-methoxyethoxy)-3a,4,5,6-tetrahydro-3H-pyrrolo[1,2-b]pyrazol-2-yl)-3-methylbenzonitrile;
2-chloro-4-((3S,3aR,4R)-4-fluoro-3-(2-fluoroethoxy)-3a,4,5,6-tetrahydro-3H-pyrrolo[1,2-b]pyrazol-2-yl)-3-methylbenzonitrile; and
2-chloro-4-((3S,3aS)-5,5-difluoro-3-(2-methoxyethoxy)-3a,4,5,6-tetrahydro-3H-pyrrolo[1,2-b]pyrazol-2-yl)-3-methylbenzonitrile.

Embodiment 13

A pharmaceutical composition comprising a therapeutically effective amount of a compound according to any one of embodiments 1 to 12 in free form or in pharmaceutically acceptable salt form and one or more pharmaceutically acceptable carriers.

Embodiment 14

A combination comprising a therapeutically effective amount of a compound according to any one of embodiments 1 to 12 in free form or in pharmaceutically acceptable salt form and one or more therapeutically active co-agents.

Embodiment 15

A compound according to any of embodiments 1 to 12 in free form or in pharmaceutically acceptable salt form for use as a medicament.

Embodiment 16

A compound according to any of embodiments 1 to 12 in free form or in pharmaceutically acceptable salt form for use in the treatment or prevention of muscular atrophy; lipodistrophy; long-term critical illness; sarcopenia; frailty or age-related functional decline; reduced muscle strength and function; reduced bone density or growth such as osteoporosis and osteopenia; the catabolic side effects of glucocorticoids; chronic fatigue syndrome; chronic myalgia; bone fracture; acute fatigue syndrome; muscle loss following elective surgery; cachexia; chronic catabolic state; eating disorders; side effects of chemotherapy; wasting secondary to fractures; wasting in connection with chronic obstructive pulmonary disease (COPD), chronic liver disease, AIDS, weightlessness, cancer cachexia, burn and trauma recovery, chronic catabolic state such as coma, eating disorders such as anorexia and chemotherapy; depression; nervousness; irritability; stress; growth retardation; reduced cognitive function; male contraception; hypogonadism; Syndrome X; diabetic complications or obesity.

Embodiment 17

A compound according to any of embodiments 1 to 12 in free form or in pharmaceutically acceptable salt form for use in the treatment or prevention of muscle wasting diseases, osteoporosis, sarcopenia, frailty, and cancer cachexia.

Embodiment 18

A method of treating a disorder or disease selected from muscular atrophy; lipodistrophy; long-term critical illness; sarcopenia; frailty or age-related functional decline; reduced muscle strength and function; reduced bone density or growth such as osteoporosis and osteopenia; the catabolic side effects of glucocorticoids; chronic fatigue syndrome; chronic myalgia; bone fracture; acute fatigue syndrome; muscle loss following elective surgery; cachexia; chronic catabolic state; eating disorders; side effects of chemotherapy; wasting secondary to fractures; wasting in connection with chronic obstructive pulmonary disease (COPD), chronic liver disease, AIDS, weightlessness, cancer cachexia, burn and trauma recovery, chronic catabolic state such as coma, eating disorders such as anorexia and chemotherapy; depression; nervousness; irritability; stress; growth retardation; reduced cognitive function; male contraception; hypogonadism; Syndrome X; diabetic complications or obesity, comprising administering to the subject a therapeutically effective amount of the compound according to any one of embodiments 1 to 12 in free form or in pharmaceutically acceptable salt form.

Embodiment 19

A method according to embodiment 18, wherein the disorder or disease is selected from muscle wasting diseases, osteoporosis, sarcopenia, frailty, and cancer cachexia.

Embodiment 20

A compound of formula (III) in free form or in pharmaceutically acceptable salt form

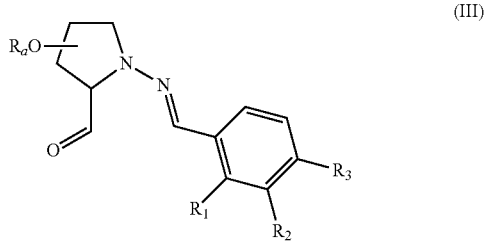

(III)

wherein $R_1$, $R_2$, $R_3$ are as defined for formula (I) and $R_a$ is a protecting group.

Embodiment 21

A compound of formula (III') or (III") in free from or in pharmaceutically acceptable salt form

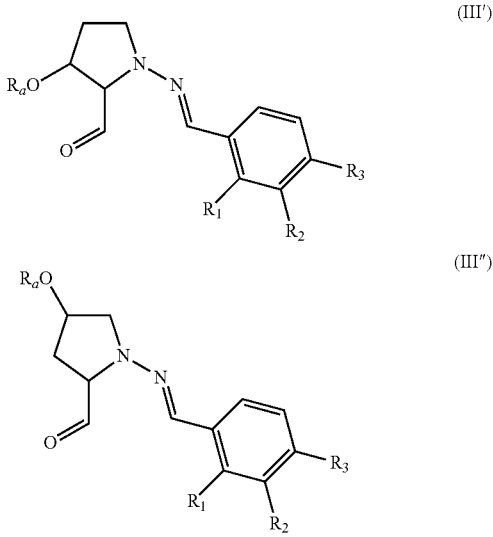

wherein $R_1$, $R_2$, $R_3$ are as defined for formula (I) and $R_a$ is a protecting group.

Embodiment 22

A compound of formula (III), (III') or (III") in free form or in pharmaceutically acceptable salt form according to embodiments 20 or 21, wherein $R_a$ is selected from t-butyldimethylsilyl (TBDMS), methoxymethyl (MOM), tetrahydropyranyl (THP), t-butyldiphenylsilyl (TBDPS).

Embodiment 23

Use of a compound of formula (III), (III') or (III") as defined in any of embodiments 20 to 22 in free form or in pharmaceutically acceptable salt form in the manufacture of a compound of formula (I) as defined in embodiment 1 in free form or in pharmaceutically acceptable salt.

Embodiment 24

Process for the preparation of a compound of formula (I) as defined in embodiment 1, in free from or in pharmaceutically acceptable salt form, comprising a) the ring closure of a compound of the formula (III), (III') or (III") as defined in any of embodiments 20 to 22 in free form or in salt form in the presence of a suitable solvent and a suitable Lewis acid to give a compound of formula (II)

b) the optional reduction, oxidation and/or other functionalization of the resulting compound of formula (II)

c) the cleavage of any protecting group(s) optionally present d) the recovery of the so obtainable compound of formula (I) in free form or in pharmaceutically acceptable salt form.

The invention claimed is:

1. A compound of formula (I) in free form or in pharmaceutically acceptable salt form,

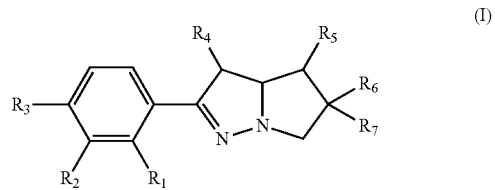

(I)

wherein $R_1$ is $C_1$-$C_3$alkyl;

$R_2$ is halogen;

$R_3$ is cyano;

$R_4$ is selected from amino, halogen, hydroxy, $C_1$-$C_3$alkyl, halogen-$C_1$-$C_3$alkyl, hydroxy-$C_1$-$C_3$alkyl, $C_3$-$C_6$cycloalkyl, $C_1$-$C_3$alkoxy, halogen-$C_1$-$C_3$alkoxy, $C_1$-$C_3$alkoxy-$C_1$-$C_3$alkoxy, $C_3$-$C_6$cycloalkyl-$C_1$-$C_3$alkoxy, $C_3$-$C_6$cycloalkoxy; or $R_4$ is selected from a (=O), (=S) or (=N($R_8$)) group;

$R_5$ is selected from hydrogen, amino, halogen, hydroxy, $C_1$-$C_3$alkyl, halogen-$C_1$-$C_3$alkyl, hydroxy-$C_1$-$C_3$alkyl, $C_3$-$C_6$cycloalkyl, $C_1$-$C_3$alkoxy, halogen-$C_1$-$C_3$alkoxy, $C_3$-$C_6$cycloalkoxy; or $R_5$ is selected from a (=O), (=S) or (=N($R'_8$)) group;

$R_6$ is selected from hydrogen, amino, halogen, hydroxy, $C_1$-$C_3$alkyl, halogen-$C_1$-$C_3$alkyl, $C_3$-$C_6$cycloalkyl, $C_1$-$C_3$alkoxy, halogen-$C_1$-$C_3$alkoxy, $C_3$-$C_6$cycloalkoxy;

$R_7$ is selected from hydrogen, halogen, halogen-$C_1$-$C_3$alkyl;

or $R_6$ and $R_7$ together with the carbon to which they are attached form a —C(=O)— or —C(=S)— group;

$R_8$ and $R'_8$ are independently selected from hydrogen, hydroxy;

provided $R_5$, $R_6$, and $R_7$ are not all hydrogen.

2. A compound of formula (Ia) according to claim 1 in free from or in pharmaceutically acceptable salt form

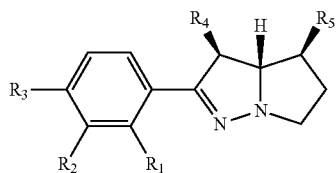

wherein $R_1$, $R_2$, $R_3$, $R_4$ and $R_5$ are as defined in claim 1, wherein $R_5$ is not hydrogen.

3. A compound of formula (Ib) according to claim 1 in free from or in pharmaceutically acceptable salt form

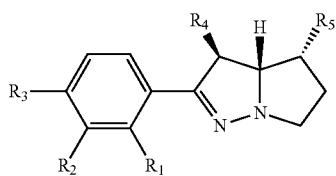

wherein $R_1$, $R_2$, $R_3$, $R_4$ and $R_5$ are as defined in claim 1, wherein $R_5$ is not hydrogen.

4. A compound of formula (Ic) according to claim 1 in free from or in pharmaceutically acceptable salt form

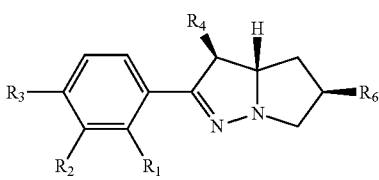

wherein $R_1$, $R_2$, $R_3$, $R_4$ and $R_6$ are as defined in claim 1, wherein $R_6$ is not hydrogen.

5. A compound of formula (Id) according to claim 1 in free form or in pharmaceutically acceptable salt form

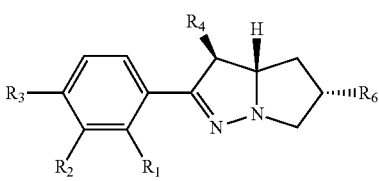

wherein $R_1$, $R_2$, $R_3$, $R_4$ and $R_6$ are as defined in claim 1, wherein $R_6$ is not hydrogen.

6. A compound according to claim 1 in free form or in pharmaceutically acceptable salt form,
wherein
$R_1$ is methyl; $R_2$ is chloro; $R_3$ is cyano.

7. A compound according to claim 1 in free form or in pharmaceutically acceptable salt form, wherein $R_4$ is selected from hydroxy, $C_1$-$C_3$alkoxy.

8. A compound according to claim 1 in free form or in pharmaceutically acceptable salt form, wherein $R_5$ if present is selected from halogen, hydroxy.

9. A compound according to claim 1 in free form or in pharmaceutically acceptable salt form, wherein $R_6$ if present is selected from halogen, hydroxy.

10. A compound according to claim 1 in free form or in pharmaceutically acceptable salt form, wherein $R_7$ if present is hydrogen.

11. A compound according to claim 1 in free form or in pharmaceutically acceptable salt form, which is selected from
  2-chloro-4-(4-hydroxy-3-methoxy-3a,4,5,6-tetrahydro-3H-pyrrolo[1,2-b]pyrazol-2-yl)-3-methylbenzonitrile;
  2-chloro-4-(3,4-dihydroxy-3a,4,5,6-tetrahydro-3H-pyrrolo[1,2-b]pyrazol-2-yl)-3-methylbenzonitrile;
  2-chloro-4-(3-ethoxy-4-hydroxy-3a,4,5,6-tetrahydro-3H-pyrrolo[1,2-b]pyrazol-2-yl)-3-methylbenzonitrile;
  2-chloro-4-(4-hydroxy-3-isopropoxy-3a,4,5,6-tetrahydro-3H-pyrrolo[1,2-b]pyrazol-2-yl)-3-methylbenzonitrile;
  2-chloro-4-(5-hydroxy-3-methoxy-3a,4,5,6-tetrahydro-3H-pyrrolo[1,2-b]pyrazol-2-yl)-3-methylbenzonitrile;
  2-chloro-4-(3-methoxy-5-oxo-3a,4,5,6-tetrahydro-3H-pyrrolo[1,2-b]pyrazol-2-yl)-3-methylbenzonitrile;
  2-chloro-4-(3,5-dihydroxy-3a,4,5,6-tetrahydro-3H-pyrrolo[1,2-b]pyrazol-2-yl)-3-methylbenzonitrile;
  2-chloro-4-(5-hydroxy-3-methoxy-5-(trifluoromethyl)-3a,4,5,6-tetrahydro-3H-pyrrolo[1,2-b]pyrazol-2-yl)-3-methylbenzonitrile;
  2-chloro-4-(4-fluoro-3-methoxy-3a,4,5,6-tetrahydro-3H-pyrrolo[1,2-b]pyrazol-2-yl)-3-methylbenzonitrile;
  2-chloro-4-(5-fluoro-3-methoxy-3a,4,5,6-tetrahydro-3H-pyrrolo[1,2-b]pyrazol-2-yl)-3-methylbenzonitrile;
  2-chloro-4-(5,5-difluoro-3-methoxy-3a,4,5,6-tetrahydro-3H-pyrrolo[1,2-b]pyrazol-2-yl)-3-methylbenzonitrile;
  2-chloro-4-(3-(2-fluoroethoxy)-4-hydroxy-3a,4,5,6-tetrahydro-3H-pyrrolo[1,2-b]pyrazol-2-yl)-3-methylbenzonitrile;
  2-chloro-4-(3-(cyclopropylmethoxy)-4-hydroxy-3a,4,5,6-tetrahydro-3H-pyrrolo[1,2-b]pyrazol-2-yl)-3-methylbenzonitrile;
  2-chloro-4-(5-iodo-3-methoxy-3a,4,5,6-tetrahydro-3H-pyrrolo[1,2-b]pyrazol-2-yl)-3-methylbenzonitrile;
  2-chloro-4-(3,4-dimethoxy-3a,4,5,6-tetrahydro-3H-pyrrolo[1,2-b]pyrazol-2-yl)-3-methylbenzonitrile;
  2-chloro-4-(4-hydroxy-3-(2-methoxyethoxy)-3a,4,5,6-tetrahydro-3H-pyrrolo[1,2-b]pyrazol-2-yl)-3-methylbenzonitrile;
  2-chloro-4-(4-fluoro-3-(2-methoxyethoxy)-3a,4,5,6-tetrahydro-3H-pyrrolo[1,2-b]pyrazol-2-yl)-3-methylbenzonitrile;
  2-chloro-4-(4-fluoro-3-(2-fluoroethoxy)-3a,4,5,6-tetrahydro-3H-pyrrolo[1,2-b]pyrazol-2-yl)-3-methylbenzonitrile and
  2-chloro-4-(5,5-difluoro-3-(2-methoxyethoxy)-3a,4,5,6-tetrahydro-3H-pyrrolo[1,2-b]pyrazol-2-yl)-3-methylbenzonitrile.

12. A compound according to claim 11 in free form or in pharmaceutically acceptable salt form which is selected from
  2-chloro-4-((3S,3aS,4S)-4-hydroxy-3-methoxy-3a,4,5,6-tetrahydro-3H-pyrrolo[1,2-b]pyrazol-2-yl)-3-methylbenzonitrile;
  2-chloro-4-((3S,3aS,4R)-4-hydroxy-3-methoxy-3a,4,5,6-tetrahydro-3H-pyrrolo[1,2-b]pyrazol-2-yl)-3-methylbenzonitrile;
  2-chloro-4-((3S,3aS,4S)-3-ethoxy-4-hydroxy-3a,4,5,6-tetrahydro-3H-pyrrolo[1,2-b]pyrazol-2-yl)-3-methylbenzonitrile;

2-chloro-4-((3S,3aS,4R)-3-ethoxy-4-hydroxy-3a,4,5,6-tetrahydro-3H-pyrrolo[1,2-b]pyrazol-2-yl)-3-methylbenzonitrile;

2-chloro-4-((3S,3aR,4R)-4-fluoro-3-methoxy-3a,4,5,6-tetrahydro-3H-pyrrolo[1,2-b]pyrazol-2-yl)-3-methylbenzonitrile;

2-chloro-4-((3S,3aR,4S)-4-fluoro-3-methoxy-3a,4,5,6-tetrahydro-3H-pyrrolo[1,2-b]pyrazol-2-yl)-3-methylbenzonitrile;

2-chloro-4-((3S,3aS)-5,5-difluoro-3-methoxy-3a,4,5,6-tetrahydro-3H-pyrrolo[1,2-b]pyrazol-2-yl)-3-methylbenzonitrile;

2-chloro-4-((3S,3aS,5S)-5-iodo-3-methoxy-3a,4,5,6-tetrahydro-3H-pyrrolo[1,2-b]pyrazol-2-yl)-3-methylbenzonitrile;

2-chloro-4-((3S,3aS,4S)-3,4-dimethoxy-3a,4,5,6-tetrahydro-3H-pyrrolo[1,2-b]pyrazol-2-yl)-3-methylbenzonitrile;

2-chloro-4-((3S,3aS,4S)-4-hydroxy-3-(2-methoxyethoxy)-3a,4,5,6-tetrahydro-3H-pyrrolo[1,2-b]pyrazol-2-yl)-3-methylbenzonitrile;

2-chloro-4-((3S,3aR,4R)-4-fluoro-3-(2-methoxyethoxy)-3a,4,5,6-tetrahydro-3H-pyrrolo[1,2-b]pyrazol-2-yl)-3-methylbenzonitrile;

2-chloro-4-((3S,3aR,4R)-4-fluoro-3-(2-fluoroethoxy)-3a,4,5,6-tetrahydro-3H-pyrrolo[1,2-b]pyrazol-2-yl)-3-methylbenzonitrile; and 2-chloro-4-((3S,3aS)-5,5-difluoro-3-(2-methoxyethoxy)-3a,4,5,6-tetrahydro-3H-pyrrolo[1,2-b]pyrazol-2-yl)-3-methylbenzonitrile.

13. A pharmaceutical composition comprising a therapeutically effective amount of a compound according to claim 1 in free form or in pharmaceutically acceptable salt form and one or more pharmaceutically acceptable carriers.

14. A combination comprising a therapeutically effective amount of a compound according to claim 1 in free form or in pharmaceutically acceptable salt form and one or more therapeutically active co-agents.

15. A method of treating a disorder or disease selected from muscle wasting diseases, osteoporosis, sarcopenia, frailty, and cancer cachexia, comprising administering to the subject a therapeutically effective amount of the compound according to claim 1 in free form or in pharmaceutically acceptable salt form.

* * * * *